US006908929B2

(12) United States Patent
Breitenbucher et al.

(10) Patent No.: US 6,908,929 B2
(45) Date of Patent: Jun. 21, 2005

(54) PHENYL-SUBSTITUTED IMIDAZOPYRIDINES

(75) Inventors: J. Guy Breitenbucher, Escondido, CA (US); Nicholas I. Carruthers, Poway, CA (US); Xiaobing Li, San Diego, CA (US); Laura C. McAtee, San Diego, CA (US); Chandravadan R. Shah, San Diego, CA (US); Ronald L. Wolin, San Diego, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/821,244

(22) Filed: Mar. 29, 2001

(65) Prior Publication Data

US 2002/0006934 A1 Jan. 17, 2002

Related U.S. Application Data

(60) Provisional application No. 60/272,121, filed on Feb. 28, 2001, and provisional application No. 60/194,071, filed on Mar. 31, 2000.

(51) Int. Cl.$^7$ .............................................. A01N 43/42
(52) U.S. Cl. .................... 514/300; 514/212; 514/233.2; 514/253; 540/597; 544/127; 544/362; 546/121
(58) Field of Search ........................... 546/121; 544/127, 544/362; 540/597; 514/233.2, 212, 300, 253

(56) References Cited

U.S. PATENT DOCUMENTS

| 4,727,145 A | 2/1988 | Press |
| 4,833,149 A | 5/1989 | Press |
| 4,861,897 A | 8/1989 | Press et al. |
| 4,880,824 A | 11/1989 | Press et al. |
| 5,182,291 A | 1/1993 | Gubin et al. |
| 5,352,707 A | 10/1994 | Pompni et al. |
| 5,385,912 A | 1/1995 | Neuenschwander et al. |
| 5,681,954 A | 10/1997 | Yamamoto et al. |

FOREIGN PATENT DOCUMENTS

| EP | 0 289 371 A1 | 11/1988 |
| EP | 0 978 512 A1 | 2/2000 |
| JP | 52 113992 A1 | 9/1997 |
| WO | WO 95/30659 A1 | 11/1995 |
| WO | WO 97/43271 A1 | 11/1997 |
| WO | WO 98/18797 A1 | 5/1998 |
| WO | WO 98/06703 A1 | 11/1998 |
| WO | WO 98/48797 A1 | 11/1998 |
| WO | WO 99/32115 A1 | 7/1999 |
| WO | WO 99/33822 A1 | 7/1999 |
| WO | WO 01/74815 A2 | 10/2001 |
| WO | WO 01/10050 A1 | 1/2002 |

OTHER PUBLICATIONS

Agarwal, Shiv K. et al., "Synthesis and pharmacological activities of 1–(2,4–disubstituted phenoxy)–3–[N1–N4–arylplperazinyl)]propan es and 1–(4–chlorobenzoyl)–3–substituted 6–methoxy–2–a4–[3–N1–(N4–phenylpiperazinyl)propoxy]phenyluindoles", Indian J. Chem., Sect. B (1991), 30B(4), 413–16.

Joshi, Krishna C. et al., "Preparation of new fluorine containing 2–phenylindole derivatives as antifertility agents", J. Indian Chem. Soc. (1985), 62(5), 388–90.

Takeuchi, K. et al., "1,2–disubstituted indole, azaindole and benzimidazole derivatives possessign amine moiety: a novel series of thrombin inhibitors" Bioorg. Med. Chem. Lett. (2000), 10(20), 2347–2351.

Walczynski, Krzysztof et al., "Non–imidatole histamine H3 ligands, part 2: New 2–substituted benzothiazoles as histamine H3 antagonists", Archiv de Phamazie, vol. 332, No. 11, Nov. 1999, pp. 389–398.

Walczynski, Krzysztof et al., "Non–imidazole histamine H3 liquids. Part I. Synthesis of 2–(1–Piperazinyl)–and 2–(hexahydro–1H, 4–diazepin–1–yl) benzothiazole derivatives as H3–antagonists with H1 blocking activities", Biosciences Information Services, Farmco, vol. 54, No. 10, Oct. 30, 1999, pp. 684–694.

Muro, Tomio et al. "Aralkylamine Derivatives" Database Abstract, XP–002182516, Sep. 24, 1977.

Srivastava, Pratima et al. "Potential inhibitors of plasmodial heme oxygenase; an innovative approach for combating chloroquine resistant malaria"—Bioorganic & Medicinal Chemistry, 6 (1998) pp. 181–187.

International Search Report dated of Nov. 28, 2001.

Mario D. Bachi and Eric Bosch, "On the Mechanism of Reductive Degradation of Dithiocarbonates by Tributylstannane", J. Chem. Soc. Perkin Trans, 1988, pp 1517–1519. Dept. of Organic Chemistry, The Weizmann Institute of Science, Rehovot 76100, Israel.

Christopher Blackburn, "A Three–Compound Solid–Hase Synthesis of 3–Aminoimidazo[1,2–alpha]azines", Tetrahedron Letters, vol. 39, 1998 pp 5469–5472. Published by Elsevier Science Ltd. 1998.

Christopher Blackburn, Bing Guan, Paul Fleming, Kazumi Shiosaki and Shirling Tsai, "Parellel Synthesis of 3–Aminoimidazol[1,2–alpha]ptyridines and pyrazines by a New Three–Compound Condensation", Tetrahedron Letters, vol. 39, 1998 pp 3635–3638. Published by Elsevier Science Ltd. 1998.

Alan J. Chalk and Steven A. Magennis, "Palladium–Catalyzed Vinyl Substitution Reactions. I. A New Synthesis of 2–and 3–Phenyl Substituted Allylic Alcohols, Aldehydes and Ketones from Allylic Alcohols", J. Org. Chem., vol. 41, No. 2, 1976, pp 273–278. Givaudan Corporation, Clifton, New Jersey 07014.

Cecile Enguehard, Jean–Louis Renou, Valerie Collot, Maud Hervet, Sylvain Rault and Alain Gueiffier, "Reactivity of 3–Iodoimidazo[1,2–alpha]pyridines Using a Suzuki–Type Cross–Coupling Reaction", J. Org. Chem. vol. 65, 2000, pp 6572–6575.

(Continued)

Primary Examiner—Bernard Dentz

(57) ABSTRACT

The invention features pharmaceutically-active imidazopyridines and derivatives that are substituted with phenyl, methods of making them, and methods of using them.

21 Claims, No Drawings

OTHER PUBLICATIONS

C. Robin Ganellin, Fabien Leurquin, Antonia Piripitsi, Jean-Michel Arrang, Monique Garbarg, Xavier Ligneau, Walter Schunack and Jean–Charles Schwartz, "Synthesis of Potent Non–imidazole Histamine H3–Receptor Antagonists", Arch. Pharm. Pharm. Med. Chem., vol. 331, 1998, pp 395–404. Wiley–VCH Verlag GmbH, D–69451 Weinheim 1998.

Kristjan S. Gudmundsson, John C. Drach and Leroy B. Townsend, "An improved Synthesis of 2–Chlorinated Imidazo[1,2–α]–Pyridines And The Application Of This Procedure For The Synthesis Of Several New Polychlorinated Imidazo[1,2–α]Pyridines", Synthetic Communications, vol. 27(10), 1997, pp 1763–1775. Coypright by Marcel Dekker, Inc.

Kristin S. Gudmundsson, John C. Drach and Leroy B. Townsend, "Synthesis of Imidazo[1,2–alpha]Pyridine C–Nucleosides with an Unexpected Site of Ribosylation", J. Org. Chem., vol. 62, 1997, pp 3453–3459. Copyright American Chemical Society 1997.

Richard F. Heck, "Palladium–Catalyzed Vinylation of Organic Hallides", Organic Reactions, vol. 27, 1989, pp 345–391, Robert E. Krieger Publishing Company, Malabar, Florida.

James J. Kaminski, James A. Bristol, Chester Puchalski, Raymond G. Lovey, Arthur J. Elliott, Henry Guzik, Daniel M. Solomon, David J. Conn, Martin S. Domalski, Shing–Chun Wong, Elijah H. Gold, James F. Long, P.J.S. Chiu, Merl Steinberg and Andrew T. McPhail, "Antiulcer Agents. 1. Gastric Antisecretory and Cytoprotective Properties of Substituted Imidazo[1,2 alpha]pyridines", J. Med. Chem., vol. 28, 1985 pp 876–892. American Chemical Society 1985.

Stephen H. Kawai, Robert J. Hambalek and George Just, "A Facile Synthesis of an Oxidation Product of Terfenadine", J. Org. Chem., vol. 59, 1994, pp 2620–2622. Dept. of Chem. McGill University, Montreal, Quebec, Canada H3A 2K6.

John B. Melpolder and Richard F. Heck, "A Palladium Catalyzed Arylation of Allylic alcohols with Aryl Halides", J. Org. Chem., vol. 41, No. 2, 1976, pp 265–272. Dept. of Chemistry, Univ. of Delaware, Newark, Delaware 19711.

Anju P. Misra, K. Raj and A.P. Bhaduri, "In Search of Imidazo[1,2–alpha]Pyridine Derivatives Exhibiting Resistance For Catalytic Hydrogenation", Synthetic Communications, vol. 29(18), 1999, pp 3227–3236. Copyright Marcel Dekker, Inc. 1999.

Marco Mor, Fabrizio Bordi, Claudia Silvia, Silvia Rivara, Patrizia Crivori, Pier Vincenzo Plazzi, Vigilio Ballabeni, Antonio Caretta, Elisabetta Barocelli, Mariannina Impicciatore, Pierre–Alain Carrupt and Bernard Testa, "H3–Receptor Antagonists: Synthesis and Structure–Activity Relationships of Para–and Meta–Substituted 4(5)–Phenyl–2–[[2–[4(5)–imidazolyl]ethyl]thio]imidazoles", J. Med. Chem., vol. 40, 1997, pp 2571–2578. Copyright American Chemical Society 1997.

Kazunari Ohta, Keizaburo Minami, Harutoshi Yoshikawa and Yasuo Ishida, "Synthesis and Herbicidal Activity of Phenoxypropionic Acid Derivatives with Imidazo[1,2–alpha]pyridine Moiety", Biosci. Biotech. Biochem., vol. 57 (11), 1993, pp 1844–1848. Agricultural Research Labs., Agro Div., Takeda Chemical Industries, Ltd., 10 Wadai, Tsukuba, Ibaraki 300 42, Japan.

William W. Paudler and Hyun G. Shin, "The Synthesis of Substituted Imidazo[1,2–α]pyridines via Ylidelike Intermediates", J. of Org. Chem., vol. 33, No. 4, Apr. 1968, pp 1638–1639. Clippinger Labs, Dept. of Chemistry, Ohio University, Athens, Ohio 45701.

Pauline J. Sanfilippo, Maud Urbanski, Jeffery B. Press, Barry Dubinsky, and John B. Moore, Jr. "Synthesis of (Aryloxy)alkylamines. 2. Novel imidazo–fused Heterocycles with Calcium Channel Blocking and Local Anesthetic Activity", J. Med. Chem., vol. 31, 1988, pp 2221–2227. Research Labs, Ortho Pharmaceutical Corporation, Raritan, New Jersey 08869.

Pauline J. Sanfilippo, Maud Urbanski, Jeffery B. Press, Zoltan G. Hajos, David A. Shriver and Cynthia K. Scott, "Synthesis of (Arloxy)alkylamines. 1. Novel Antisecretory Agents with H+ K+ –ATPase Inhibitory Activity", J. Med. Chem., vol. 31, 1988, pp 1778–1785.

Astrid Sasse, Holger Stark, Sibylle Reidemeister, Annette Huls, Sigurd Elz, Xavier Ligneau, C. Robin Ganellin, Jean-Charles Schwartz and Walter Schunack, Novel Partial Agonists for the Histamine H3 Receptor with High in Vitro and in Vivo Activity, J. Med. Chem., vol. 42, 1999, pp 4269–4274. Copyright American Chemical Society 1999.

Stephan Thorand and Norbert Krause, "Improved Procedures for the Palladium–Catalyzed Coupling of Terminal Alkynes with Aryl Bromides (Sonogashira Coupling)", J. Org. Chem., vol. 63, 1998, pp 8551–8553. American Chemical Society.

Matthew J. Tozer, Ildiko M. Buck, Tracey Cooke, S. Barret Kalindjian, Lain M. McDonaod, Michael J. Pether, Katherine I. M. Steel, "4–Chlorobenzylsulfonamide and sulfamide derivatives of histamine homologues: The Design of Potent Histamine H3 Receptor Antagonists", Bioorganic & Medicinal Chemistry Letters, vol. 9, 1999, pp 3103–3108. Published by Elsevier Science Ltd. 1999.

Giuseppe Trapani, Massimo Franco, Laura Ricciardi, Andrea Latrofa, Giuseppe Genchi, Enrico Senna, Francesca Tuveri, Elisabetta Cagetti, Giovanni Biggio and Gaetano Liso, "Synthesis and Binding Affinity of 2–Phenylimidazo [1,2–alpha]pyridine Derivatives for Both Central and Peripheral Benzodiazepine Receptors. A New Series of High–Affinity and Selective Ligands for the Peripheral Type", J. Med. Chem., vol. 40, 1997, pp 3109–3118. Copyright American Chemical Society 1997.

Giuseppe Trapani, Massimo Franco, Andrea Latrofa, Laura Ricciardi, Angelo Carotti, Mariangela Serra, Enrico Sanna, Giovanni Biggio and Gaetano Liso, "Novel 2–Phenylimidazo[1,2–alpha]pyridine Derivatives as Potent and Selective Ligands for Peripheral Benzodiazepine Receptors: Synthesis, Binding Affinity, and in Vivo Studies", J. Med. Chem., vol. 42, 1999, pp 3934–3941. Copyright American Chemical Society 1999.

PHENYL-SUBSTITUTED IMIDAZOPYRIDINES

CROSS-REFERENCE TO RELATED APPLICATIONS

This application claims priority from U.S. Provisional Application Ser. No. 60/194,071, filed on Mar. 31, 2000, and U.S. Provisional Application Ser. No. 60/272,121, filed on Feb. 28, 2001.

FIELD OF THE INVENTION

The invention relates to pharmaceutically-active fused heterobicyclic compounds and methods of using them to treat or prevent disorders and conditions, such as those mediated by the histamine $H_3$ receptor.

BACKGROUND

The histamine $H_3$ receptor is located as a presynaptic autoreceptor in the central nervous system and as a presynaptic heteroreceptor on serotonergic, noradrenergic, dopaminergic, and cholinergic neurons. The histamine $H_3$ receptor is also located peripherally in tissues such as vascular smooth muscle cells.

Proposed uses of histamine $H_3$ antagonists include the treatment or prevention of dementia, Alzheimer's disease (Panula et al. *Abstr. Society Neuroscience*, 1995, 21:1977), epilepsy (Yokoyama et al. *Eur. J. Pharmacol.*, 1993, 234:129), sleep/wake disorders (Lin et al., *Br. Res.*, 1990, 523, 325; Monti et al., *Eur. J. Pharmacol.*, 1991, 205, 283) including narcolepsy, insomnia, and jet lag, eating disorders (Machidori et al. *Brain Research*, 1992, 590:180), motion sickness, vertigo, attention deficit hyperactivity disorder, learning and memory disorders (Barnes et al. *Abstr. Society Neuroscience*, 1993, 19:1813), schizophrenia (Schlicker et al. *Naunyn Schmiedeberg's Arch. Pharmacol.*, 1996, 353:325), and sequelae associated with post-ischemic reperfusion and hypertension (Imamura et al., *J. Pharmacol. Expt. Ther.*, 1994, 271, 1259). $H_3$ antagonists are also useful to treat or prevent neurogenic inflammation such as migraine (McLeod et al., *Abstr. Society Neuroscience*, 1996, 22, 2010), asthma (Ichinose et al., *Eur. J. Pharmacol.*, 989, 174, 49), obesity, allergic rhinitis, substance abuse, bipolar disorders, manic disorders, and depression. Histamine $H_3$ antagonists alone or in combination with a histamine $H_1$ antagonist are believed to be useful in the treatment of upper airway allergic response or allergic rhinitis (see, e.g., U.S. Pat. Nos. 5,217,986, 5,352,707, and 5,869,479).

As noted, the prior art related to histamine $H_3$ ligands was comprehensively reviewed recently ("*The Histamine $H_3$ Receptor—A Target for New Drugs*", Leurs, R., and Timmerman, H., (Editors), Elsevier, 1998). Within this reference the medicinal chemistry of histamine $H_3$ agonists and antagonists was reviewed (see Krause et al. and Phillips et al., respectively). Thus the importance of an imidazole moiety containing only a single substitution in the 4 position was noted together with the deleterious effects of additional substitution on activity. Particularly methylation of the imidazole ring at any of the remaining unsubstituted positions was reported to strongly decrease activity.

More recently several publications have described histamine $H_3$ ligands that do not contain an imidazole moiety. Examples include Ganellin et al *Arch. Pharm.* (Weinheim, Ger.) 1998, 331, 395; Walczynski et al *Arch. Pharm.* (Weinheim, Ger.) 1999, 332, 389; Walczynski et al *Farmaco* 1999, 684; Linney et al *J. Med. Chem.* 2000, 2362; U.S. Pat. No. 5,352,707; PCT Application WO99/42458, published Aug. 26, 1999; and European Patent Application 0978512, published on Feb. 9, 2000.

SUMMARY OF THE INVENTION

The invention features phenyl-substituted imidazopyridine compounds, methods of making them, and methods of using them. One aspect of the invention provides compounds of the following formula (I)(A):

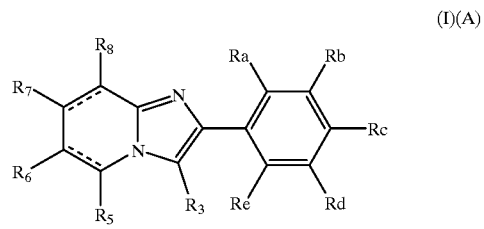

(I)(A)

wherein both dashed lines are present to form carbon-carbon double bonds; or both dashed lines are absent;

$R_3$ is H, $C_{1-6}$ alkyl, phenyl, or benzyl;

each of $R_5$, $R_6$, $R_7$ and $R_8$ is independently H, $C_{1-6}$ alkyl, $C_{1-6}$ alkoxy, halo, or amino;

one of $R_a$, $R_b$, $R_c$, $R_d$, and $R_e$ is —WYZ and the others are independently selected from H, $C_{1-6}$ alkyl, $C_{1-6}$ alkoxy, halo, and amino;

W is $R_9$, O—$R_9$, $NR_{10}$, —(CO)(O)$R_9$, —N($R_{10}$)$SO_2$—$R_9$, —O(CO)$R_9$, —(CO)$NR_{10}$, or —N($R_{10}$)—CO—$R_9$, wherein $R_9$ is $C_{1-6}$ alkylene, $C_{2-6}$ alkynylene, $C_{2-6}$ alkenylene, phenylene, or $C_{2-5}$ heterocyclic bivalent radical, and $R_{10}$ is H, $C_{1-6}$ alkyl, $C_{2-8}$ alkynyl, $C_{2-8}$ alkenyl, phenyl, or $C_{2-5}$ heterocyclic radical;

Y is absent, $C_{1-6}$ alkylene, $C_{2-8}$ alkynylene, $C_{2-6}$ alkenylene, or bivalent $C_{1-8}$ alkoxy;

Z is $C_{2-8}$ heterocyclic radical with at least one basic nitrogen atom in the ring, optionally including in the ring up to 3 additional heteroatoms or moieties independently selected from O, C=O, N, NH, NG, S, SO, and $SO_2$, wherein G is $R_{15}$, $COR_{15}$, $COOR_{15}$, $SO_2R_{15}$, $SO_2N$ or $CSR_{15}$; or Z is $NR_{11}R_{12}$ where each of $R_{11}$ and $R_{12}$ is independently selected from H, $C_{1-6}$ alkyl, phenyl, benzyl, $C_{3-8}$ cycloalkyl, and $C_{2-5}$ heterocyclic radical; and $R_{15}$ is $C_{1-6}$ alkyl, $C_{2-8}$ alkynyl, $C_{2-6}$ alkenyl, $C_{3-7}$ cycloalkyl, or $C_{4-7}$ cycloalkenyl;

provided that where $R_c$ is $WNR_{11}R_{12}$, each of $R_{11}$ and $R_{12}$ being independently selected from $C_{1-6}$ alkyl, then at least one of the following is true: $R_b$ or $R_d$ is alkyl, alkoxy, amino, or halo; the dashed lines represent one carbon-carbon double bond or are absent; $R_a$ or $R_e$ is alkyl, alkoxy, amino, or halo; or W is —$R_9$—, —$NR_{10}$—, —(CO)(O)$R_9$—, —O (CO)$R_9$—, —(CO)$NHR_9$—, or —N($R_{10}$)(CO)$R_9$—;

and further provided that where each of $R_a$, $R_b$, $R_d$, and $R_e$ is H, and W is a straight chain, unsubstituted alkoxy, then at least one of the following is true: Z is cyclic; the dashed lines represent one carbon-carbon double bond or are absent; or $R_7$ or $R_8$ is alkyl, alkoxy, halo, or amino;

and further provided that where each of $R_a$, $R_b$, $R_d$, and $R_e$ is H, and W is a straight chain, unsubstituted propoxy, then YZ is not N-piperidyl or N-morpholinyl; and each of the above hydrocarbyl or heterocyclic groups being optionally substituted with between 1 and 3 substituents selected from $C_{1-3}$ alkyl, halo, hydroxy, $C_{2-5}$ heterocyclic radical, phenyl, and phenyl($C_{1-3}$ alkyl); and wherein each of the above heterocyclic groups may be attached to the rest of the molecule by a carbon atom or a heteroatom;

or a pharmaceutically acceptable salt, amide, ester, or hydrate thereof.

According to another aspect of the invention, the disclosed compounds of formula (I)(A) and certain other compounds represented by formula (I)(A) without the proviso that where each of $R_a$, $R_b$, $R_d$, and $R_e$ is H, and W is a straight chain, unsubstituted propoxy, then YZ is not N-piperidyl or N-morpholinyl, are useful for the treatment and/or prevention of diseases and conditions mediated by the histamine 3 ($H_3$) receptor. Examples of these other compounds include 2-(4-piperidinopropoxyphenyl)-8-methylimidazo[1,2-a]pyridine and 2-(4-morpholinopropoxyphenyl)-8-methylimidazo[1,2-a]pyridine.

A third aspect of the invention features methods of making the disclosed compounds.

Additional features of the invention are disclosed in the following description and examples, and in the appended claims.

DETAILED DESCRIPTION

The invention features pharmaceutically active phenyl-substituted imidazopyridines and methods of making and using them. The description is organized as follows:

A. Terms
B. Compounds
C. Synthetic Methods
D. Uses
E. Synthetic Chemical Examples
F. Biological Examples
G. Other Embodiments
H. Claims A. Terms The following terms are defined below and by their usage throughout this disclosure.

"Alkyl" includes straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl does not include cycloalkyl.

"Alkenyl" includes straight chain and branched hydrocarbon radicals as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl does not include cycloalkenyl.

"Alkynyl" include straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

"Alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and $SO_2$.

"Aryl" includes phenyl, naphthyl, biphenylyl, and so on.

"Cycloalkyl" includes cyclopropyl, cyclobutyl, cyclopentyl, cyclohexyl, cycloheptyl, cyclooctyl, and so on.

"Cycloalkenyl" includes cyclobutenyl, cyclobutadienyl, cyclopentenyl, cyclopentadienyl, cyclohexenyl, cyclohexadienyl, cyclohexatrienyl (phenyl), cycloheptenyl, and so on. "Cycloalkynyl" includes the analogous rings with one or more triple bonds.

"Heterocyclic radicals" include aromatic and nonaromatic rings having carbon atoms and at least one heteroatom (O, S, N) or heteroatom moiety ($SO_2$, CO, CONH, COO) in the ring. Unless otherwise indicated, a heterocyclic radical may have a valence connecting it to the rest of the molecule through a carbon atom, such as 3-furyl or 2-imidazolyl, or through a heteroatom, such as N-piperidyl or 1-pyrazolyl. Examples of heterocyclic radicals include thiazoylyl, furyl, pyranyl, isobenzofuranyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolyl, furazanyl, pyrrolidinyl, pyrrolinyl, imdazolidinyl, imidazolinyl, pyrazolidinyl, pyrazolinyl, piperidyl, piperazinyl, indolinyl, and morpholinyl. For example, preferred heterocyclic radicals for Z include morpholinyl, piperazinyl, pyrrolidinyl, pyridyl, cyclohexylimino, cycloheptylimino, and more preferably, piperidyl.

"halo" includes fluoro, chloro, bromo, and iodo, and preferably fluoro or chloro.

"patient" or "subject" includes mammals such as humans and animals (dogs, cats, horses, rats, rabbits, mice, non-human primates) in need of observation, experiment, treatment or prevention in connection with the relevant disease or condition. Preferably, the patient is a human.

"composition" includes a product comprising the specified ingredients in the specified amounts as well as any product which results directly or indirectly from combinations of the specified ingredients in the specified amounts.

Concerning the various radicals in this disclosure and in the claims, two general remarks are made. The first remark concerns valency. As with all hydrocarbon radicals, whether saturated, unsaturated or aromatic, and whether or not cyclic, straight chain, or branched, and also similarly with all heterocyclic radicals, each radical includes substituted radicals of that type and monovalent, bivalent, and multivalent radicals as indicated by the context of the claims. The context will indicate that the substituent is an alkylene or hydrocarbon radical with at least two hydrogen atoms removed (bivalent) or more hydrogen atoms removed (multivalent). An example of a bivalent radical linking two parts of the molecule is —$CH_2$—$CH_2$—, or W in formula (I)(A) which links Z with the phenyl group Ar and thus, subject to the claims, W can be an alkyl (strictly, alkylene) group (—Ar—$CH_2CH_2CH_2$—Z), an aminoalkyl group (—Ar—NH—$CH_2CH_2CH_2$—Z), an alkoxy group (—Ar—O—$CH_2CH_2CH_2$—Z), an "oxa" (—Ar—O—Z), a covalent bond (—Ar—Z), and so on.

Second, radicals or structure fragments as defined herein are understood to include substituted radicals or structure fragments. Using "alkyl" as an example, "alkyl" should be understood to include substituted alkyl having one or more substitutions, such as between 1 and 5, 1 and 3, or 2 and 4 substituents. The substituents may be the same (dihydroxy, dimethyl), similar (chlorofluoro), or different (chlorobenzylor aminomethyl-substituted). Examples of substituted alkyl include haloalkyl (such as fluoromethyl, chloromethyl, difluoromethyl, perchloromethyl, 2-bromoethyl, and 3-iodocyclopentyl), hydroxyalkyl, aminoalkyl, nitroalkyl, alkylalkyl, and so on.

Preferred substitutions for Ar include methyl, methoxy, trifluoromethoxy, difluoromethoxy, fluoromethoxy, fluoromethyl, difluoromethyl, perfluoromethyl (trifluoromethyl), 1-fluoroethyl, 2-fluoroethyl, ethoxy, fluoroethoxy, fluoro, chloro, and bromo, and particularly methyl, fluoromethyl, perfluoro, trifluoromethoxy, difluoromethoxy, methoxy, and fluoro.

Examples of other substituted radicals or fragments include 1-methyl-2-pyrrolidino, 4-(piperidyl)-piperidyl, [4-(N-benzyl)piperidyl]amino, 4-fluorobenzylamino, beta-hydroxyethoxy, beta-hydroxypropoxy, 2-oxo-pyrrolidino, 4-(1-methyl-4-piperidinyl), 4-(5-methyl-thiazoyl), 4-chlorobenzyl, 4-fluorobenzyl, and 4-methylbenzyl.

B. Compounds

One aspect of the invention features compounds of formula (I) as described in the Summary section above.

Preferred compounds of formula (I) include those compounds wherein: (a) Z comprises piperidyl, morpholinyl, benzyl amino, phenyl amino, substituted benzyl amino, piperazinyl, pyrrolidyl, or a $C_{6-8}$ cycloalkylimino radical; (b) Z is $NR_{11}R_{12}$ where each of $R_{11}$ and $R_{12}$ is independently selected from H, $C_{1-4}$ alkyl, phenyl, and benzyl; (c) W is hydroxy-substituted bivalent $C_{2-4}$ alkoxy, bivalent $C_{2-4}$ alkoxy, bivalent $C_{2-4}$ alkylamino, butenylene, or butynylene; (d) W comprises propoxy, ethoxy, propylamino, or ethylamino; and $R_7$ or $R_8$ is methyl; (e) $R_7$ is methyl; (f) at least one of $R_a$, $R_b$, $R_d$, and $R_e$ is methyl; (g) each of $R_5$, $R_6$, $R_7$ and $R_8$ is independently H, methyl, ethyl, methoxy, ethoxy, halomethyl, fluoro, or chloro (and preferably halomethyl, methyl or fluoro); or wherein one of $R_a$, $R_b$, $R_c$, $R_d$, and $R_e$ is WZ and the others are independently selected from H, methyl, ethyl, methoxy, ethoxy, halomethyl, fluoro, or chloro (and preferably halomethyl, methyl or fluoro); or both; (h) the dashed lines are two carbon-carbon double bonds (for example, between C-5 and C-6 and between C-7 and C-8 to form an imidazopyridine skeleton); (i) the dashed lines are absent, thereby forming a tetrahydroimidazopyridine skeleton; (j) $R_a$ or $R_e$ is methyl, fluoro, or methoxy; (k) provided that where each of $R_a$, $R_b$, $R_d$, and $R_e$ is H, and W is a straight chain, unsubstituted bivalent alkoxy, then at least two of the following are true: Z is cyclic; at least one of the dashed lines is absent; or $R_7$ or $R_8$ is methyl; (l) provided that where $R_c$ is $WNR_{11}R_{12}$, each of $R_{11}$ and $R_{12}$ being independently selected from $C_{1-6}$ alkyl, then at least two of the following are true: $R_b$ or $R_d$ is methyl, methoxy, ethyl, ethoxy, or halo; at least one of the dashed lines is absent; $R_a$ or $R_e$ is methyl, methoxy, ethyl, ethoxy, fluoro, or chloro; or W is $R_9$, —(CO)(O)$R_9$, —O(CO)$R_9$, —(CO)NHR$_9$, —N(R$_{10}$)—CO—R$_9$, or NR$_{10}$; or combinations thereof.

Additional preferred compounds include those wherein: (m) $R_3$ is H or methyl; each of $R_b$ and $R_d$ is independently H, methyl, or methoxy; each of $R_7$ and $R_8$ is independently H, methyl, fluoro, or chloro; each of $R_5$ and $R_6$ is H; each of $R_a$ or $R_e$ is independently H, methyl, fluoro, or chloro; W is $C_{2-4}$ alkoxy, $C_4$ alkylene, $C_4$ alkynylene, $C_4$ alkenylene, , —N(R$_{10}$)SO$_2$—(C$_{1-5}$ alkyl), —(CO)O—C$_{2-3}$ alkyl, —(CO)NH—(C$_{1-3}$ alkyl), —NH(CO)(C$_{1-3}$alkyl), or NH(C$_{1-6}$alkyl); and Z is pyrrolidyl, piperidyl, morpholinyl, piperazinyl, (piperidyl)-piperidyl, or NR$_{11}$R$_{12}$ where each of R$_{11}$ and R$_{12}$ is independently selected from H, C$_{1-5}$ alkyl, phenyl, benzyl, C$_{3-8}$ cycloalkyl, and C$_{2-5}$ heterocyclic radical, but at least one of R$_{11}$ and R$_{12}$ is not H; or taken together, R$_{11}$ and R$_{12}$ with the N to which they are attached form a C$_{6-8}$ cycloalkylimino radical.

As an alternative to the proviso that "where each of $R_a$, $R_b$, $R_d$, and $R_e$ is H, and W is a straight chain, unsubstituted propoxy, then YZ is not N-piperidyl or N-morpholinyl," the invention also contemplates replacing that provision with the proviso that "where YZ is N-piperidyl or N-morpholinyl, and W is a straight chain, unsubstituted propoxy, then at least one of the following is true: at least one of $R_a$, $R_b$, $R_d$, and $R_e$ is alkoxy, alkyl, or halo; $R_8$ is not methyl or $R_7$ is not H; or the dashed lines represent one double bond or are absent."

Examples of more preferred compounds include the following: 2-[4-[3-(Piperidino) propylamino]phenyl]-7-methylimidazo[1,2-a]pyridine; (E/Z)-2-[4-[4-Piperidinobut-1-enyl]phenyl]-7-methylimidazo[1,2-a]pyridine; [4-(8-Methyl-imidazo[1,2-a]pyridin-2-yl)-phenyl]-(2-pyrrolidin-1-yl-ethyl)-amine; [4-(8-Methyl-imidazo[1,2-a]pyridin-2-yl)-phenyl]-(2-piperidyin-1-yl-ethyl)-amine; 2-[4-[4-Pyrrolidinobutyl]phenyl]-7-methylimidazo[1,2-a]pyridine; 2-[4-[2-(1-Methyl)-2-pyrrolidino]ethoxy-3-methylphenyl]imidazo[1,2-a]pyridine; and N,N-Diethyl-N'-[4-(8-methyl-imidazo[1,2-a]pyridin-2-yl)-phenyl]-propane-1,3-diamine.

Additional examples of preferred compounds include: 2-(4-Piperidinopropoxy-2-methylphenyl)-7-methylimidazo[1,2-a]pyridine; 2-(4-Cycloheptylaminopropoxyphenyl)-7-methylimidazo[1,2-a]pyridine; 2-[4-[4-Piperidinobut-1-ynyl]phenyl]-7-methylimidazo[1,2-a]pyridine; 2-(4-Pyrrolidinopropoxyphenyl)-7-methylimidazo[1,2-a]pyridine; 2-(4-Piperidinopropoxyphenyl)-7-methylimidazo[1,2-a]pyridine; 2-[4-(3-Piperidin-1-yl-propoxy)-phenyl]-imidazo[1,2-a]pyridine; 2-[4-[4-Pyrrolidinobut-1-ynyl]phenyl]-7-methylimidazo[1,2-a]pyridine; and 2-(4-Piperidinopropoxyphenyl)-8-methylimidazo[1,2-a]pyridine.

Preferred compounds include: N,N-Diethyl-N'-[4-(7-methyl-imidazo[1,2-a]pyridin-2-yl)-phenyl]-propane-1,3-diamine; 2-[4-(3-Piperidin-1-yl-propoxy)-phenyl]-5,6,7,8-tetrahydro-imidazo[1,2-a]pyridine; 7-methyl-2-[2-methyl-4-(3-piperidin-1-yl-propoxy)-phenyl]-5,6,7,8-tetrahydro-imidazo[1,2-a]pyridine; and N,N-Diethyl-N'-[4-(8-methyl-imidazo[1,2-a]pyridin-2-yl)-phenyl]-ethane-1,2-diamine. Examples of compounds which are preferred in the disclosed methods of treatment include the above compounds and compounds such as 2-(4-piperidinopropoxyphenyl)-8-methylimidazo[1,2-a]pyridine and 2-(4-morpholinopropoxyphenyl)-8-methylimidazo[1,2-a]pyridine.

Other examples of compounds, and methods of making them, are provided in the next section.

C. Synthetic Methods

The invention provides methods of making the disclosed compounds according to traditional organic synthetic methods as well as matrix or combinatorial synthetic methods. Schemes 1 through 10 describe suggested synthetic routes. Using these Schemes, the guidelines below including U.S. Pat. No. 4,727,145 and Sanfilippo, et al. *J. Med. Chem.* 188, 31, 2221 (1988), both incorporated by reference, and the examples in section E, a person of skill in the art may develop analogous or similar methods for a given compound.

Examples of the described synthetic routes include Synthetic Examples 1 through 55. Compounds analogous to the target compounds of these examples can be, and in many cases have been, made according to analogous routes. The disclosed compounds are useful in basic research, in diagnostic assays, and as pharmaceutical agents as described in the next section.

It should noted that throughout the Schemes the position of substitution is indicated by defining substituent Rc in formula 1. However it will be recognized by one skilled in the art that the substituent may be located at Ra, Rb, Rd or Re and that position Rc is chosen for illustrative purposes only.

SCHEME 1

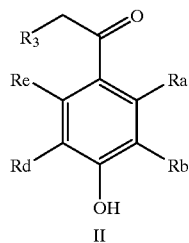
II

Step A →

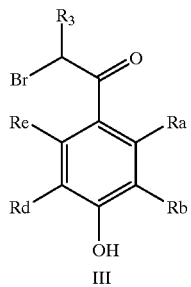
III

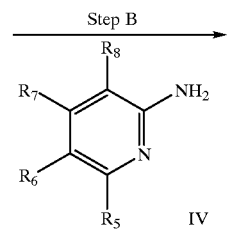
IV

Step B →

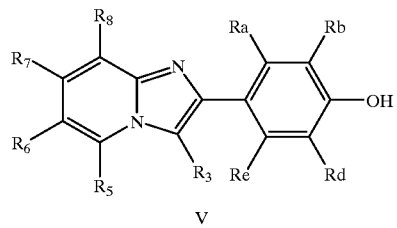
V

Compounds of formula V, wherein the substituents are as defined in formula I, may be prepared according to the process outlined in Scheme 1. Specifically a compound of formula II in Step A is treated with bromine in a solvent such as ether, chloroform, dichloromethane, carbon tetrachloride or the like, to yield a compound of formula III. The compound of formula III in Step B is reacted with a 2-aminopyridine of formula IV in a solvent such as ethanol, methanol, butanol, iso-propanol, toluene or the like at elevated temperatures, for example from 50° C. up to the boiling point of the selected solvent, preferably at from 50° C. to 75° C. to give a compound of formula V.

SCHEME 2

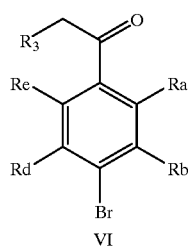
VI

Step A →

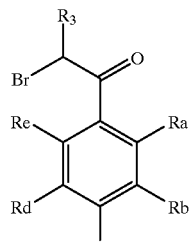
VII

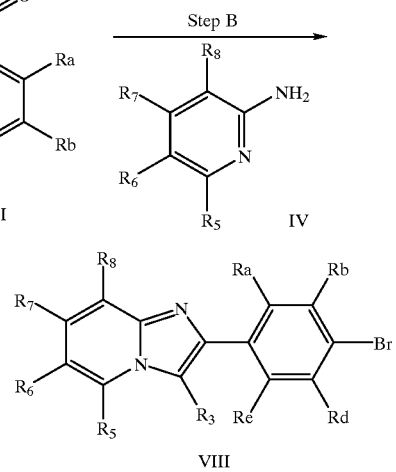
IV

Step B →

VIII

A compound of formula VIII may be prepared from a compound of formula VI as indicated in Scheme 2 using the conditions described for Steps A and B in Scheme 1.

SCHEME 3

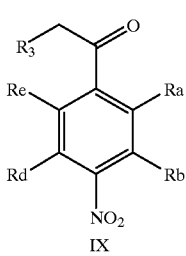
IX

Step A →

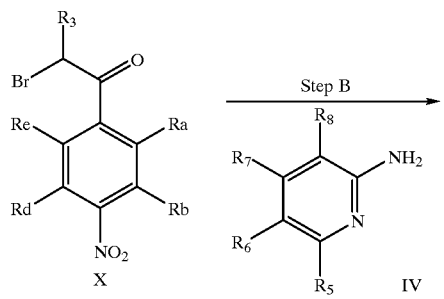
X    IV

Step B →

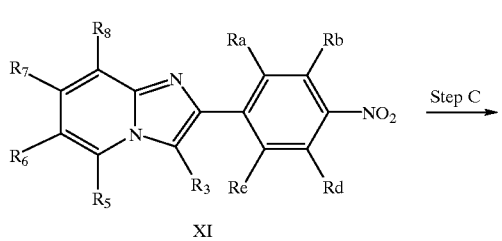
XI

Step C →

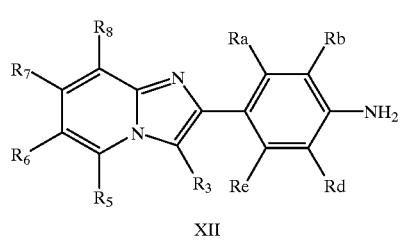

XII

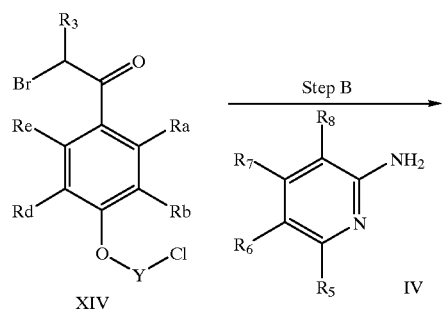

XIV

A compound of formula XII may be prepared from a compound of formula IX as shown in Scheme 3 using Steps A and B as described in Scheme I. In Step C the nitro functionality may be reduced to the corresponding amine to give compounds of formula XII. Reduction may be effected via hydrogen gas over a catalyst, for example palladium on carbon, platinum oxide, Raney nickel and the like in a solvent, for example methanol, ethanol or the like. Reduction may also be effected via transfer hydrogenation techniques, for example using cyclohexadiene as a source of hydrogen. Reduction may also be effected using zinc or iron in the presence of an acid, for example hydrochloric acid. A preferred method of reduction is transfer hydrogenation using cyclohexadiene in the presence of palladium.

XV

XVI

SCHEME 4

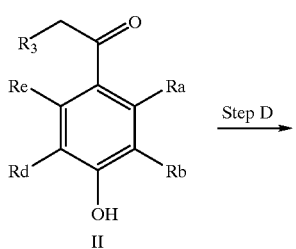

II

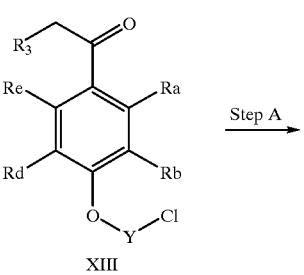

XIII

A compound of formula XVI may be prepared as shown in Scheme 4. In Step D a compound of formula II is reacted with a suitably substituted compound of formula X—Y—Cl where Y is defined and X is selected from the group consisting of Br, I, mesylate and tosylate such that under the reaction conditions a compound of formula XIII is obtained. This transformation is effected in the presence of a base, for example potassium carbonate, sodium hydroxide, triethylamine and the like, in a solvent, for example ethanol, methanol, acetone, dichloromethane, DMF, THF and the like. Preferred conditions use potassium carbonate in acetone. The compound of formula XIV may be obtained according to the procedure of Step A as described for Scheme 1. The compound of formula XV is obtained upon reacting a compound of formula XIV with a compound of formula IV according to Step B of Scheme 1. A compound of formula XVI is obtained in Step E by reacting a compound of formula XV with an amine at elevated temperature, preferably neat amine at a temperature from 50° C. to the boiling point of the amine, more preferably at about 80° C. to 100° C. Alternatively the compound of formula XV may be treated with an amine in the presence of a base, for example potassium carbonate or the like in a solvent, for example acetone at elevated temperature, for example at about 55° C.

SCHEME 5

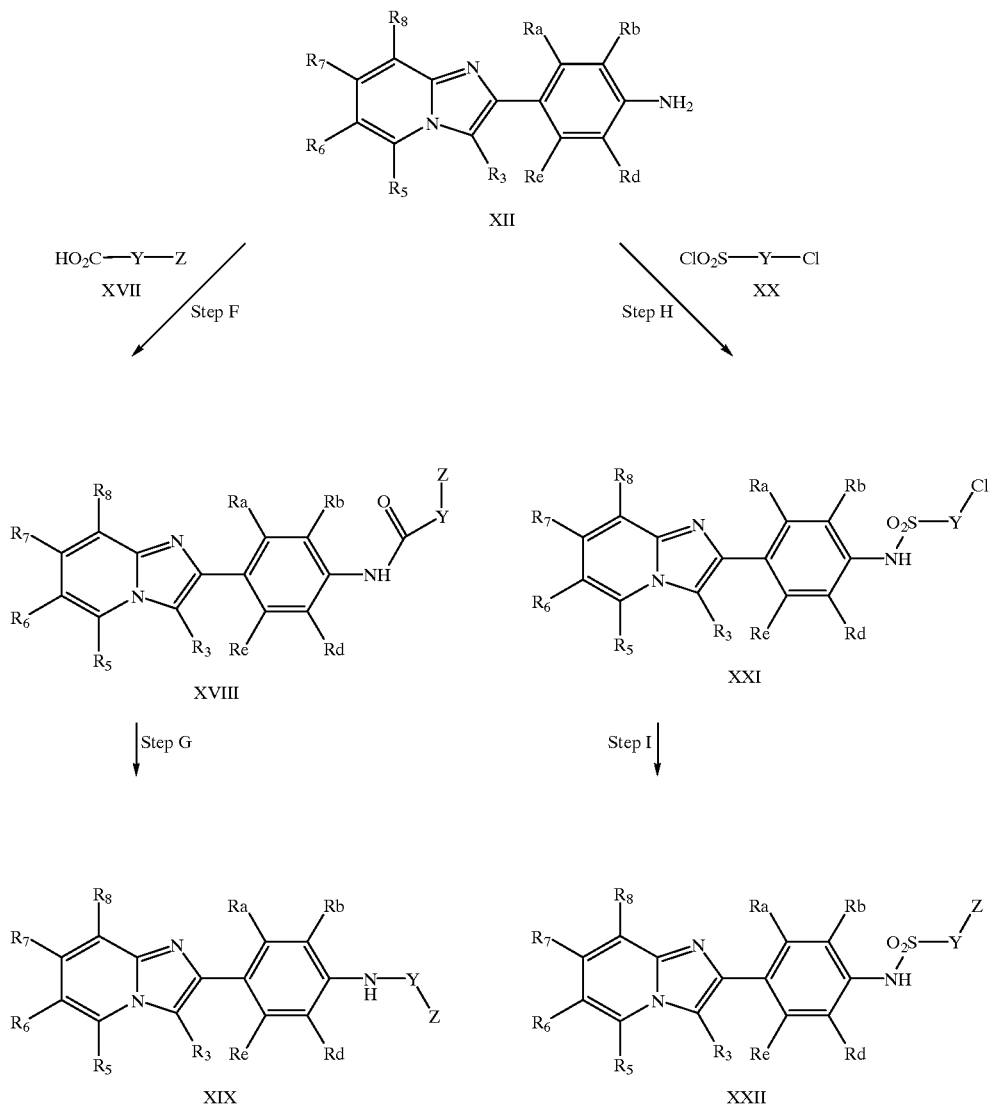

Compounds of formula XIX and XXII may be prepared according to the procedures shown in Scheme 5. Thus in Step F a compound of formula XVIII may be prepared by reacting a compound of formula XII with a carboxylic acid of formula XVII. The compound of formula XVII may initially be converted to the corresponding acid chloride or active ester by known methods and then reacted with the compound of formula XII in a solvent such as dichloromethane, THF and the like. A preferred method involves the conversion of a compound of formula XVII to the corresponding active ester upon treatment with 1-hydroxybenzotriazole in the presence of a carbodiimide, for example dicyclohexylcarbodiimide or 1-ethyl-3-(3'-dimethylaminopropyl)-carbodiimide hydrochloride in the presence of a base such as triethylamine or N,N-diisopropylethylamine to give a compound of formula XVIII. In Step G the compound of formula XVIII may be reduced to give a compound of formula XIX. Suitable reducing agents include lithium aluminum hydride, alane, sodium borohydride in the presence of acid and borane. A preferred method for the reduction of XVII to XIX is borane-methylsulfide complex in toluene. A compound of formula XXII may be prepared from a compound of formula XII as shown in Scheme 5. Thus in Step H a compound of formula XII is reacted with a sulfonyl chloride of formula XX in a solvent, for example THF, DMF and the like. A compound of formula XXII is obtained by reacting a compound of formula XXI in Step I with an amine according to the procedures described for Step E in Scheme 4.

SCHEME 6

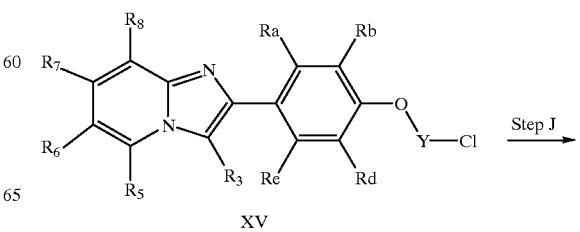

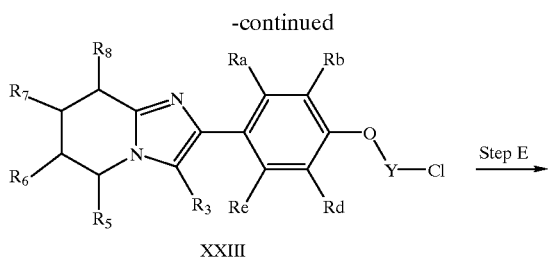

XXIII

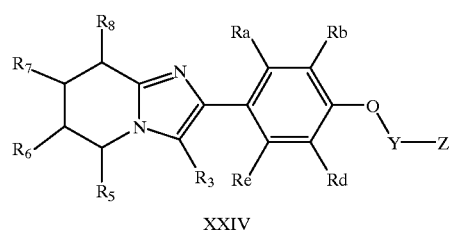

XXIV

A compound of formula XXIV may be prepared according to the process outlined in Scheme 6. A compound of formula XV may be reduced in Step J to give a compound of formula XXIII. This transformation may be effected using hydrogenation over a catalyst, for example hydrogen over platinum oxide in a solvent, for example ethanol, methanol or the like, at a pressure from 30 to 80 psi. A preferred method uses platinum oxide catalyst in ethanol at 40 to 50 psi. A compound of formula XXIV may be obtained by reacting a compound of formula XXIII with an amine according to the procedures described for Step E in Scheme 4.

SCHEME 7

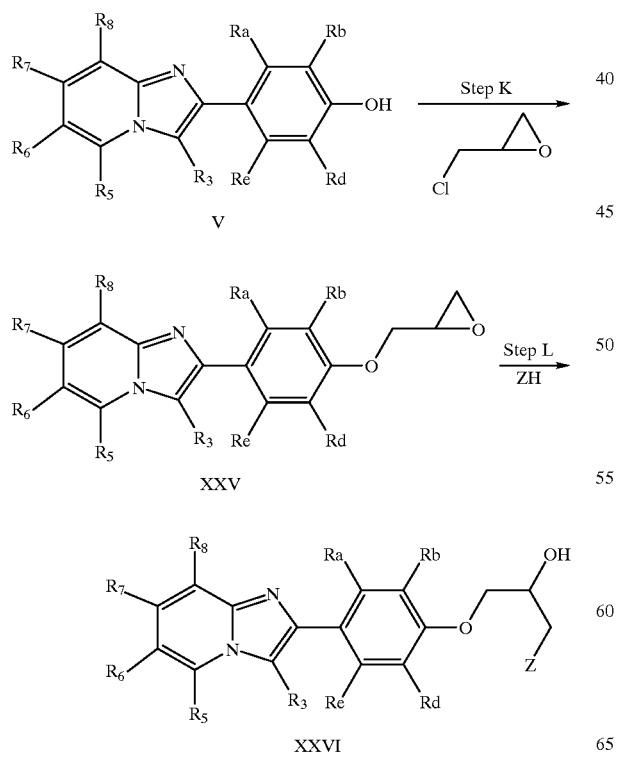

Compounds of formula XXVI may be prepared according to Scheme 7 by reacting a compound of formula V in Step K with epichlorohydrin in a solvent, for example methanol, ethanol or the like, in the presence of a base, for example sodium hydroxide or potassium hydroxide or the like. A compound of formula XXVI may be obtained from a compound of formula XXV according to Step L by treating a compound of formula XXV with an amine, ZH, at elevated temperature, for example 80° C. to 140° C., if desired in the presence of a solvent, for example 2-methoxyethylether, di(ethyleneglycol)ethylether or the like.

SCHEME 8

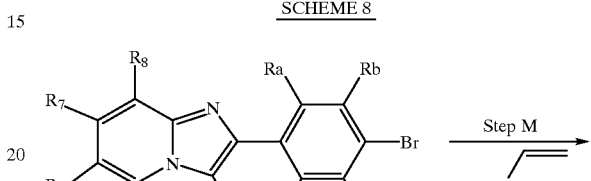

VIII

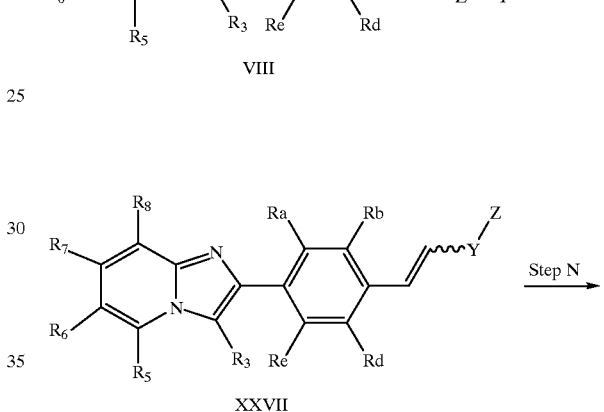

XXVII

XXVIII

Compounds of formula XXVIII may be prepared according to Scheme 8. In Step M a compound of formula VIII is reacted with the appropriate terminal alkene, of general formula indicated, in the presence of a base, for example triethylamine or N,N-diisopropylethylamine, in the presence of triphenylphosphine and a palladium catalyst, for example palladium acetate, in a solvent such as DMF, at elevated temperature to afford a compound of formula XXVII. A compound of formula XXVIII may be obtained according to Step N. Thus a compound of formula XXVII may be subjected to hydrogenation over a catalyst, for example platinum oxide, in a solvent such as methanol, ethanol or the like, at elevated pressure, for example 40 to 70 psi.

SCHEME 9A

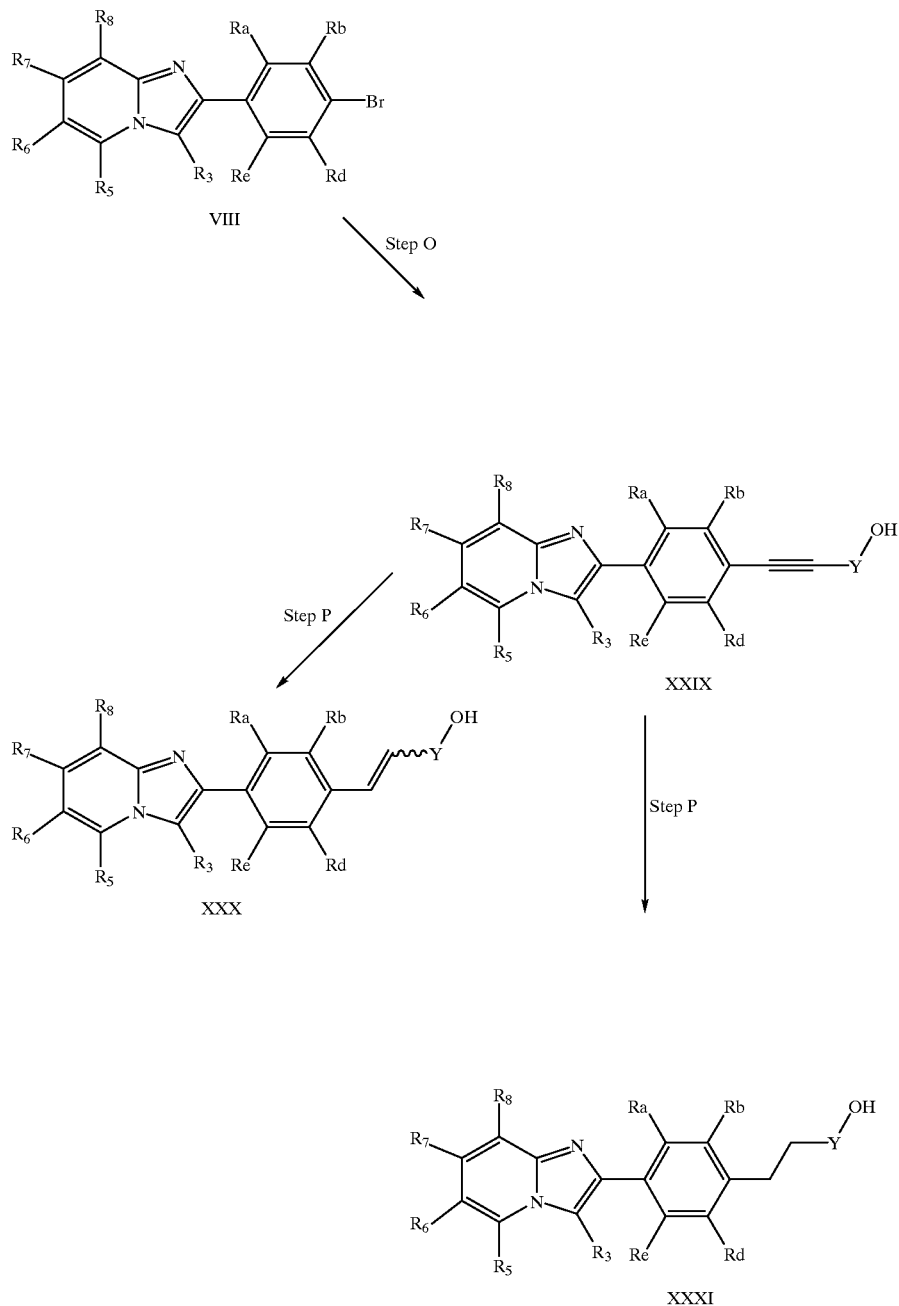

Compounds of formula XXX and XXXI may be prepared from compounds of formula VIII according to Scheme 9A. In Step O a compound of formula VIII is reacted with a terminal acetylene in the presence of a catalyst, for example tetrakis(triphenylphosphine)palladium or the like in a solvent such as acetonitrile or the like, in the presence of copper(I)iodide, to give a compound of formula XXIX. A compound of formula XXIX may be converted to a compound of formula XXX and/or formula XXXI according to Step P upon hydrogenation over palladium on barium sulfate, nickel acetate with sodium borohydride (P2 nickel), Lindlars catalyst, palladium on carbon or the like in ethanol, methanol or the like. It would be recognized that the appropriate choice of reaction conditions will favor a compound of a particular formula.

SCHEME 9B

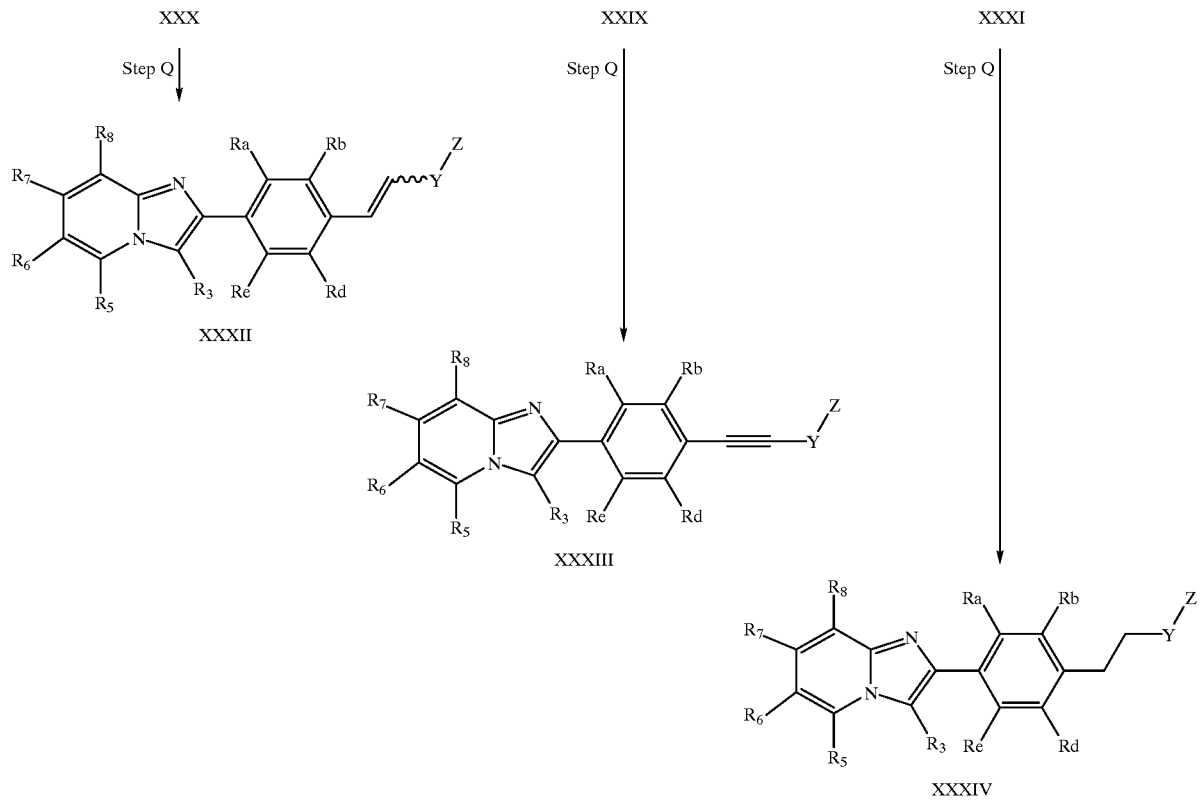

Compounds of formula XXXII, XXXIII and XXXIV may be prepared as shown in Scheme 9B according to Step Q. Thus the hydroxyl functionality of compounds XXX, XXIX and XXXI may be converted into a leaving group, for example a chloride, bromide, iodide, mesylate, tosylate or the like. In a preferred embodiment the compounds of formula XXX, XXIX and XXXI are converted to the corresponding mesylates upon treatment with methanesulfonyl chloride, in a solvent, for example dichloromethane, THF or the like, in the presence of a base, for example triethylamine, potassium carbonate or the like. The mesylate, or other leaving group, may be displaced under the conditions of Step E, Scheme 4. For example upon treatment with an amine, in acetonitrile, in the presence of potassium carbonate.

SCHEME 10

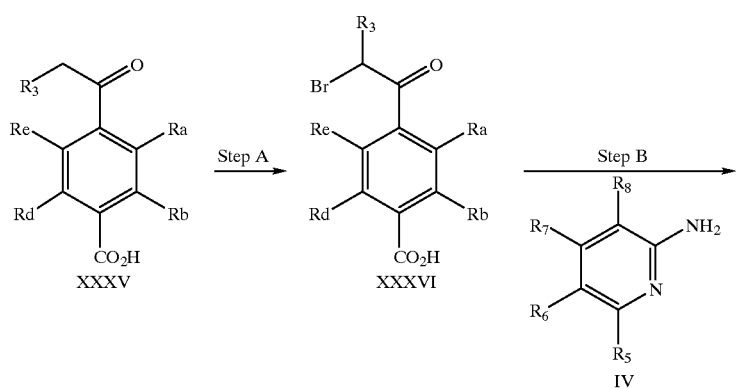

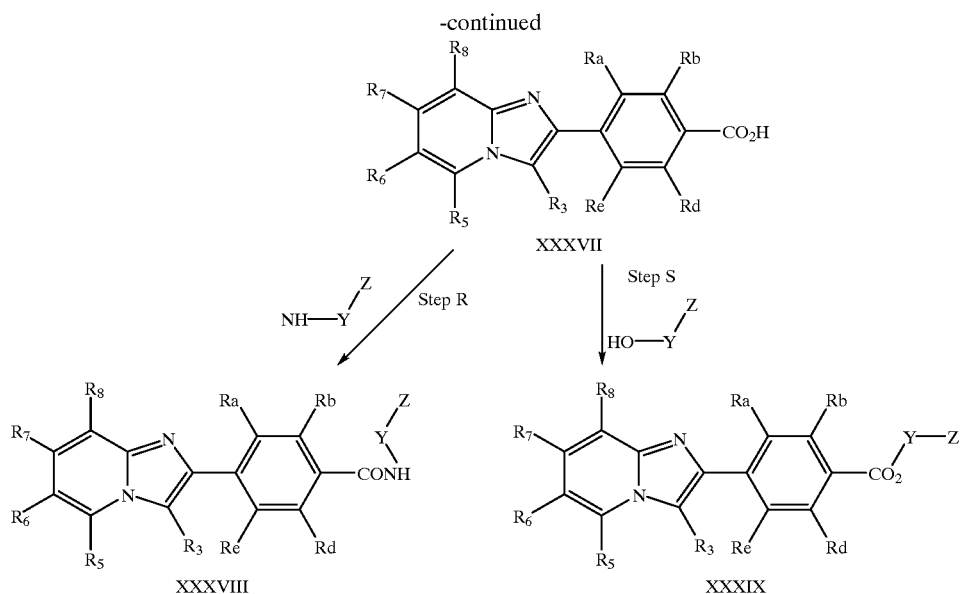

Compounds of formula XXXVIII and XXXIX may be prepared from compounds of formula XXXV. Thus compounds of formula XXXVII may be prepared from compounds of formula XXXV using the procedures of Steps A and B of Scheme 1. Compounds of formula XXXVIII may be prepared from compounds of formula XXXVII according to Step R using conventional methods of amide bond formation. For example the carboxyl group of compound XXXVII may be activated as an active ester, acid chloride, anhydride, mixed anhydride, carbonic mixed anhydride or the like and treated with an amine containing group to give a compound of formula XXXVIII. In a preferred method a compound of formula XXXVII is treated with carbonyl diimidazole in a solvent such as THF, ether or the like, followed by an amine component. A compound of formula XXXIX may be prepared according to the procedure of Step S whereupon a compound of formula XXXVII is activated and then condensed with an alcohol containing moiety to afford a compound of formula XXXIX. In a preferred embodiment a compound of formula XXXVII in dichloromethane is treated with N,N'-dicyclohexylcarbodiimide, in the presence of a base such as N,N-dimethylaminopyridine to give a compound of formula XXXIX.

D. Uses

According to the invention, the disclosed compounds and compositions are useful for the amelioration of symptoms associated with, the treatment of, and/or the prevention of, the following conditions and diseases, or symptoms associated with them: dementia, Alzheimer's disease, narcolepsy, eating disorders, motion sickness, vertigo, attention deficit hyperactivity disorder, learning and memory disorders, schizophrenia, mild cognitive impairment, upper airway allergic response (allergic rhinitis), insomnia, jet lag, obesity, asthma, neurogenic inflammation, substance abuse, bipolar disorders, manic disorders, and depression. The invention also features pharmaceutical compositions, which include, without limitation, one or more of the disclosed compounds, and a pharmaceutically acceptable carrier or excipient.

1. Dosages

Those skilled in the art will be able to determine, according to known methods, the appropriate dosage for a patient, taking into account factors such as age, weight, general health, the type of symptoms requiring treatment, and the use of other medications. An effective amount means that amount of pharmaceutical reagent (such as a prodrug, metabolic precursor, or active compound) that elicits the biological or medical response desired. In general, a therapeutically effective amount will be between 0.01 and 1000 mg/kg per day, preferably between 0.01 and 250 mg/kg body weight, and daily dosages will be between 0.50 and 5000 mg for an adult subject of normal weight. Capsules, tablets or other formulations (such as liquids and film-coated tablets) may be of between 0.20 and 100 mg, such as 0.20, 0.50, 1, 2, 3, and 10 mg can be administered according to the disclosed methods.

2. Formulations

Dosage unit forms include tablets, capsules, pills, powders, granules, aqueous and nonaqueous oral solutions and suspensions, and parenteral solutions packaged in containers adapted for subdivision into individual doses. Dosage unit forms can also be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels or cream), and by inhalation (a buccal or nasal spray) as appropriate depending on the overall health and condition of the patient as determined by a physician or veterinary doctor.

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j) propellants.

Compositions may also contain adjuvants such as preserving, wetting, emulsifying, and dispensing agents;

antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

3. Combination Therapy

The present invention also provides compositions and methods useful for the treatment of disorders or conditions modulated, preferably antagonized, by the histamine $H_3$ receptor in combination with compounds that modulate other receptors including, but not limited to, histamine $H_1$ and histamine $H_2$ receptors. The present invention includes compounds and compositions useful in methods of combination therapy for the treatment of diseases or conditions modulated by the histamine $H_3$ receptor in combination with compounds that are selective serotonin re-uptake inhibitors (SSRIs), such as PROZAC™, or are selective norepinephrine uptake inhibitors. Such combination methods include (a) administering the two or more pharmaceutical agents separately formulated and at separate times, and (b) administering the two or more agents simultaneously in a single formulation or in separate formulations administered more or less at the same time. For example, one aspect is a method of treatment comprising administering at least one histamine $H_3$ receptor modulating compound disclosed herein and administering at least one compound selected from a histamine $H_1$ receptor modulating compound, a histamine $H_2$ receptor modulating compound, a selective serotonin reuptake inhibitor (such as PROZAC™), or a selective norepinephrine uptake inhibiting compound.

4. Related Compounds

The invention provides the disclosed compounds and closely related, pharmaceutically acceptable forms of the disclosed compounds, such as salts, esters, amides, acids, hydrates or solvated forms thereof; masked or protected forms; and racemic mixtures, or enantiomerically or optically pure forms.

Pharmaceutically acceptable salts, esters, and amides include carboxylate salts (e.g., $C_{1-8}$alkyl, cycloalkyl, aryl, heteroaryl, or non-aromatic heterocyclic) amino acid addition salts, esters, and amides which are within a reasonable benefit/risk ratio, pharmacologically effective and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See example, S. M. Berge, et al., "Pharmaceutical Salts," *J. Pharm. Sci.*, 1977, 66:1-19 which is incorporated herein by reference. Representative pharmaceutically acceptable amides of the invention include those derived from ammonia, primary $C_{1-6}$ alkyl amines and secondary di ($C_{1-6}$ alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$alkyl primary amines, and di ($C_{1-2}$ alkyl)amines. Representative pharmaceutically acceptable esters of the invention include $C_{1-7}$alkyl, $C_{5-7}$cycloalkyl, phenyl, and phenyl($C_{1-6}$)alkyl esters. Preferred esters include methyl esters.

The invention also includes disclosed compounds having one or more functional groups (e.g., hydroxyl, amino, or carboxyl) masked by a protecting group. See, e.g., Greene and Wuts, *Protective Groups in Organic Synthesis*, $3^{rd}$ ed., (1999) John Wiley & Sons, N.Y. Some of these masked or protected compounds are pharmaceutically acceptable; others will be useful as intermediates. Synthetic intermediates and processes disclosed herein, and minor modifications thereof, are also within the scope of the invention.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyidiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(Imidazol-1-ylmethyl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate)

Carbonates

Examples of carbonate protecting groups include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate (tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate Sulfonates Examples of sulfonates include sulfate, methanesulfonate (mesylate), benzylsulfonate, and tosylate.

Protection for 1,2- and 1,3-Diols

Cyclic Acetals and Ketals

Examples of cyclic acetals and ketals include imethylene, ethylidene, 1-t-butylethylidene, 1-phenylethylidene, (4-methoxyphenyl)ethylidene, 2,2,2-trichloroethylidene, acetonide (isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Examples of cyclic ortho esters include methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino)benzylidene derivative, and 2-oxacyclopentylidene.

Silyl Derivatives

Examples of silyl derivatives include di-t-butylsilylene group, and 1,3-(1,1,3,3-tetraisopropyldisiloxanylidene) derivative.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl) ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido) benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl) ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of amides include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl) propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special—NH Protective Groups

Examples of special NH protective groups include

N-Alkyl and N-Aryl Amines

N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-di (4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl) mesityl]methylene, and N-(N',N'-dimethylaminomethylene).

Protection for the Carbonyl Group

Acyclic Acetals and Ketals

Examples of acyclic acetals and ketals include dimethyl, bis(2,2,2-trichloroethyl), dibenzyl, bis(2-nitrobenzyl) and diacetyl.

Cyclic Acetals and Ketals

Examples of cyclic acetals and ketals include 1,3-dioxanes, 5-methylene-1,3-dioxane, 5,5-dibromo-1,3-dioxane, 5-(2-pyridyl)-1,3-dioxane, 1,3-dioxolanes, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, O,O'-phenylenedioxy and 1,5-dihydro-3H-2,4-benzodioxepin.

Acyclic Dithio Acetals and Ketals

Examples of acyclic dithio acetals and ketals include S,S'-dimethyl, S,S'-diethyl, S,S'-dipropyl, S,S'-dibutyl, S,S'-dipentyl, S,S'-diphenyl, S,S'-dibenzyl and S,S'-diacetyl.

Cyclic Dithio Acetals and Ketals

Examples of cyclic dithio acetals and ketals include 1,3-dithiane, 1,3-dithiolane and 1,5-dihydro-3H-2,4-benzodithiepin.

Acyclic Monothio Acetals and Ketals

Examples of acyclic monothio acetals and ketals include O-trimethylsilyl-S-alkyl, O-methyl-S-alkyl or -S-phenyl and O-methyl-S-2-(methylthio)ethyl.

Cyclic Monothio Acetals and Ketals

Examples of cyclic monothio acetals and ketals include 1,3-oxathiolanes.

Miscellaneous Derivatives

O-Substituted Cyanohydrins

Examples of O-substituted cyanohydrins include O-acetyl, O-trimethylsilyl, O-1-ethoxyethyl and O-tetrahydropyranyl.

Substituted Hydrazones

Examples of substituted hydrazones include N,N-dimethyl and 2,4-dinitrophenyl.

Oxime Derivatives

Examples of oxime derivatives include O-methyl, O-benzyl and O-phenylthiomethyl.

Imines

Substituted Methylene Derivatives, Cyclic Derivatives

Examples of substituted methylene and cyclic derivatives include oxazolidines, 1-methyl-2-(1'-hydroxyalkyl) imidazoles, N,N'-dimethylimidazolidines, 2,3-dihydro-1,3-benzothiazoles, diethylamine adducts, and methylaluminum bis(2,6-di-t-butyl-4-methylphenoxide)(MAD)complex.

Protection for the Carboxyl Group

Esters

Examples of esters include the following.

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl) ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters

Examples of stannyl esters include triethylstannyl and tri-n-butylstannyl.

Amides and Hydrazides

Amides

Examples of amides include N,N-dimethyl, pyrrolidinyl, piperidinyl, 5,6-dihydrophenanthridinyl, o-nitroanilides, N-7-nitroindolyl, N-8-Nitro-1,2,3,4-tetrahydroquinolyl, and p-P-benzenesulfonamides.

Hydrazides

Examples of hydrazides include N-phenyl and N,N'-diisopropyl hydrazides.

E. SYNTHETIC CHEMICAL EXAMPLES

The following examples were prepared according to the Schemes herein, and also using guidance provided by U.S. Pat. No. 4,727,145 and San filippo, et al. *J. Med. Chem.* 188, 31, 2221 (1988).

EXAMPLE 1

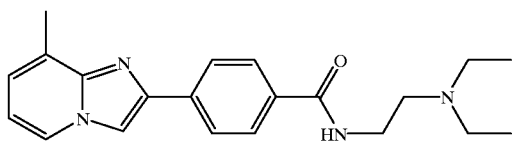

N-(2-Diethylamino-ethyl)-4-(8-methyl-imidazo[1,2-a]pyridin-2-yl)-benzamide $K_i$=90 nM Analysis: Calc'd for $C_{21}H_{26}N_4O_3HCl$ $0.5H_2O$; C, 6.45; H, 53; N, 11.95. Found: C, 6.63; H, 53.74; N, 11.66

EXAMPLE 2

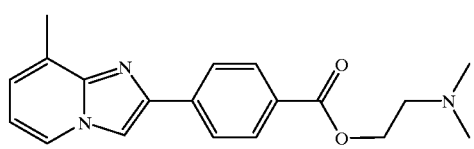

4-(8-Methyl-imidazo[1,2-a]pyridin-2-yl)-benzoic acid 2-dimethylamino-ethyl ester $K_i$=89 nM Analysis: Calc'd for $C_{19}H_{21}N_3O_2$ 3HCl; C, 5.59; H, 53.73; N, 9.71. Found: C, 5.59; H, 52.99; N, 9.8

EXAMPLE 3

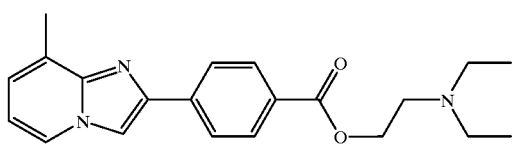

4-(8-Methyl-imidazo[1,2-a]pyridin-2-yl)-benzoic acid 2-diethylamino-ethyl ester $K_i$=20 nM Analysis: Calc'd for $C_{21}H_{25}N_3O_2$ 2HCl; C, 6.41; H, 59.44; N, 9.9. Found: C, 6.52; H, 59.7; N, 9.55

EXAMPLE 4

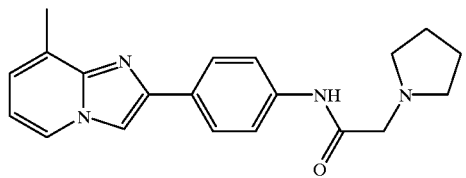

N-[4-(8-Methyl-imidazo[1,2-a]pyridin-2-yl)-phenyl]-2-pyrrolidin-1-yl-acetamide $K_i$=70 nM Analysis: Calc'd for $C_{20}H_{22}N_4O$ 2HCl; C, 5.94; H, 58.97; N, 13.75. Found: C, 5.54; H, 59.27; N, 13.42

EXAMPLE 5

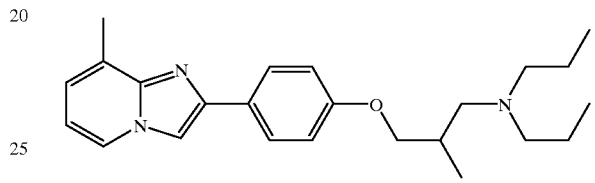

{2-Methyl-3-[4-(8-methyl-imidazo[1,2-a]pyridin-2-yl)-phenoxy]-propyl}-dipropyl-amine $K_i$=50 nM Analysis: Calc'd for $C_{24}H_{33}N_3O$ 3HCl; C, 7.42; H, 58.96; N, 8.59. Found: C, 7.63; H, 58.7; N, 8.4

Example 6

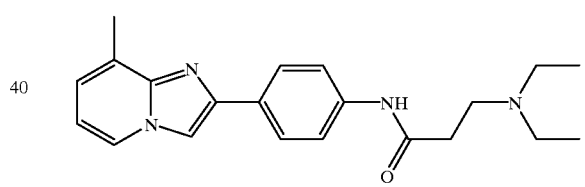

3-Diethylamino-N-[4-(8-methyl-imidazo[1,2-a]pyridin-2-yl)-phenyl]-propionamide $K_i$=55 nM Analysis: Calc'd for $C_{21}H_{26}N_4O$ 2HCl; C, 6.67; H, 59.58; N, 13.23. Found: C, 6.86; H, 59.78; N, 12.96

EXAMPLE 7

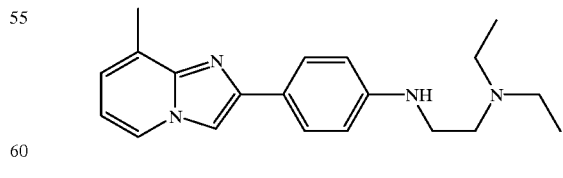

N,N-Diethyl-N'-[4-(8-methyl-imidazo[1,2-a]pyridin-2-yl)-phenyl]-ethane-1,2-diamine $K_i$=4 nM Analysis: Calc'd for $C_{20}H_{26}N_4O$ 3HCl; C, 6.77; H, 55.63; N, 12.97. Found: C, 6.62; H, 55.92; N, 12.8

EXAMPLE 8

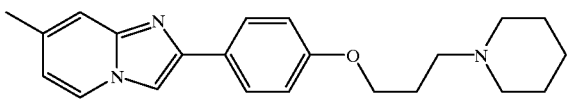

2-(4-Piperidinopropoxyphenyl)-7-methylimidazo[1,2-a]pyridine $K_i$=1 nM

Step A Preparation of p-chloropropoxyacetophenone

A mixture of p-hydroxyacetophenone (15 g) and 1-bromo-3-chloropropane (12 mL) in acetone (200 mL) was treated with potassium carbonate (17 g). The mixture was stirred at reflux temperature for 18 hours. The reaction was cooled to ambient temperature and filtered. The filtrate was concentrated in vacuo. The residue was dissolved in ether, washed with water, dried over sodium sulfate, filtered and evaporated to yield the title compound (23 g).

Step B Preparation of Alpha-bromo-4-chloropropoxyacetophenone

A solution of the product of Step A (2.0 g) in ether (10 mL) was treated with bromine (0.48 mL) and the mixture stirred for 18 hours. The mixture was poured into saturated sodium bicarbonate solution (50 mL) and the organic layer was separated. The aqueous layer was washed with a fresh portion of ether (50 mL) and the combined organic layers were washed with brine (50 mL), dried over magnesium sulfate, filtered, and evaporated to yield the title compound (2.7 g).

Step C Preparation of 2-(4-chloropropoxyphenyl)-7-methylimidazo[1,2-a]pyridine

A solution of the product of Step B (2.0 g) and 2-amino-4-picoline (0.74 g) in ethanol (8 mL) was heated at reflux temperature for 2 hours. The reaction mixture was cooled to ambient temperature and the solvent evaporated in vacuo. The residue was dissolved in dichloromethane (75 mL), washed with saturated sodium bicarbonate (2×75 mL), brine (75 mL), dried over magnesium sulfate, filtered and evaporated. The residue was purified via silica gel chromatography (ethyl acetate/hexane) to give the title compound (1.3 g).

Step D Preparation of 2-(4-Piperidinopropoxyphenyl)-7-methylimidazo[1,2-a]pyridine The product of Step C (0.2 g) and piperidine (2.0 mL) were heated at reflux temperature for 5 hours. The reaction was cooled to ambient temperature and partitioned between ethyl acetate (10 mL) and saturated sodium bicarbonate solution (10 mL). The aqueous portion was extracted with additional ethyl acetate (10 mL) and the organic portions combined. The organic portions were dried over magnesium sulfate, filtered and evaporated. The residue was purified via silica gel chromatography (dichloromethane/methanol) to give the title compound (0.21 g). This compound can also be named as 7-(methyl-2-[4-(3-piperidin-1-yl-propoxy)-phenyl]-imidazo[1,2-a]pyridine. Treatment with 2M HCl in ether afforded the dihydrochloride. $^1$H NMR (CD$_3$OD) δ 8.67 (d, J=7.5 Hz, 1H), 8.41 (s, 1H), 7.84 (m, 2H), 7.71 (s, 1H), 7.36 (dd, J=6.9 Hz, J=1.4 Hz, 1H), 7.16 (m, 2H), 4.22 (t, J=5.8 Hz, 2H), 3.64 (d, J=12.5 Hz, 2H), 3.35 (m, 2H), 3.04 (m, 2H), 2.62 (s, 3H), 2.34 (m, 2H), 1.99 (m, 2H), 1.86 (m, 3H), 1.59 (m, 1H); $^{13}$C NMR (CD$_3$OD) δ 161.0, 147.1, 141.1, 136.2, 128.5, 128.2, 120.3, 119.3, 115.8, 110.6, 109.9, 65.8, 55.0, 53.8, 24.5, 23.6, 22.1, 21.2, MS (M+H)=350.2 Analysis: Calc'd for C$_{22}$H$_{27}$N$_3$O.2HCl.(2H$_2$O) C, 57.64; H, 7.26; N, 9.17; Found: C, 57.68; H, 7.13; N, 9.16.

EXAMPLE 9

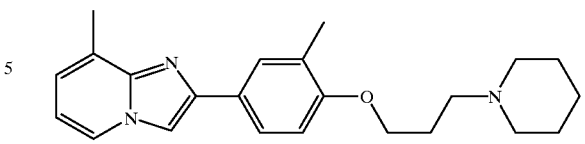

2-(4-Piperidinopropoxy-3-methylphenyl)-8-methylimidazo[1,2-a]pyridine $K_i$=32 nM Step A Preparation of p-chloropropoxy-3-methylacetophenone A mixture of p-hydroxy-3-methylacetophenone (4.7 g) and 1-bromo-3-chloropropane (12 mL) in methanol (20 mL) was treated with potassium hydroxide (5.3 g). The mixture was stirred at reflux temperature for 16 hours. The solvent was evaporated in vacuo and the residue partitioned between water (20 mL) and ether (50 mL). The organic fraction was washed with water (3×20 mL), dried over sodium sulfate, filtered and evaporated to give the crude material containing the title compound that was used without further purification.

Step B Preparation of alpha-bromo-4'-chloropropoxy-3-methylacetophenone

A solution of the product of Step A (6.7 g) in ether (80 mL) was treated with bromine (16 mL) and the mixture stirred for 14 hours. The mixture was poured into saturated sodium bicarbonate solution (100 mL). The organic layer was separated, washed with additional saturated sodium bicarbonate solution (100 mL), water (100 mL), dried over sodium sulfate, filtered and evaporated to give the crude material containing the title compound that was used without further purification.

Step C Preparation of 2-(4'-chloropropoxy-3-methylphenyl)-8-methylimidazo[1,2-a]pyridine A solution of the product of Step B (9 g) and 2-amino-3-picoline (3 g) in ethanol (40 mL) was heated at reflux temperature for 4 hours. The reaction mixture was cooled to ambient temperature and the solvent evaporated in vacuo. The residue was purified via silica gel chromatography (ethyl acetate/hexane) to give the title compound (2.8 g).

Step D Preparation of 2-(4-Piperidylpropoxy-3-methylphenyl)-8-methylimidazo[1,2-a]pyridine The product of Step C (0.5 g) and piperidine (8 mL) were heated at reflux temperature for 12 hours. The reaction was cooled to ambient temperature and the excess piperidine was removed in vacuo. The residue was dissolved in ethyl acetate (100 mL) and washed with water, dried over magnesium sulfate, filtered and evaporated. The residue was purified via silica gel chromatography (dichloromethane/methanol) to give the title compound (0.4 g). MS (ESI) m/z 364.2 (MH$^+$); $^1$H NMR (400 MHz, CDCl$_3$) δ 7.96 (d, J=6.5 Hz, 1H), 7.74 (t, J=6.2 Hz, 3H), 6.90 (dd, J=6.7 and 8.4 Hz, 2H), 6.65 (t, J=6.8 Hz, 1H), 4.05 (t, J=6.7 Hz, 2H), 2.66 (s, 3H), 2.54 (t, J=7.4 Hz, 2H), 2.43 (bs, 4H), 2.29 (s, 3H), 2.02 (m, 2H), 1.61 (m, 4H), 1.45 (m, 2H).

EXAMPLE 10

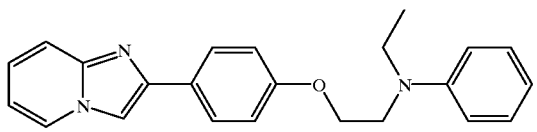

2-(4-(N-Ethyl)anilinoethoxyphenyl)imidazo[1,2-a]pyridine $K_i$=611 nM

Step A Preparation of alpha-bromo-4-hydroxyacetophenone

Bromine (1 7.6 g, 1 10 mmol) was added dropwise to a 0° C. solution of 4-hydroxyacetophenone (15 g, 110 mmol) in ether (200 mL) over 20 minutes. The mixture was stirred for 1 hour. and poured carefully into saturated sodium bicarbonate solution (500 mL). The organics were washed with saturated sodium bicarbonate solution, dried over magnesium sulfate and concentrated in vacuo. The crude product was then recrystallized from ether to afford the title compound (14.1 g).

Step B Preparation of 2-(4-hydroxyphenyl)-7-methylimidazo[1,2a]pyridinehydrobromide The product of Step A (430 mg, 2.0 mmol), and 2-picoline (188 mg, 2.0 mmol) were mixed in 2-propanol (4.0 mL) and stirred for 18 hr. The resulting crystals were collected and washed with 2-propanol and dried under vacuum to afford the title compound (287 mg).

Step C Preparation of 2-(4-(N-(ethyl)anilinoethoxy)phenyl)imidazo[1,2-a]pyridine A mixture of immobilized triphenylphisphine resin (300 mg, 0.9 meq (Fluka)), and the product of Step B (84 mg, 0.30 mmol) in tetrahydrofuran (2.5 mL) was treated with 2-(N-ethylanilino)ethanol (149 mg, 0.9 μmol) followed by diethyl azidodicarboxylate (0.142 mL, 0.9 mmol). The reaction was shaken for 20 hr. and filtered. The filtrate was concentrated in vacuo and the residue purified by silica gel chromatography (hexane/ethyl acetate) to afford the title compound (34 mg). MS (ESI) m/z 358 (MH$^+$); $^1$H-NMR (CDCl$_3$) δ 8.14 (d, 1H), 7.90 (d, 2H), 7.80 (s, 1H), 7.66 (bd, 1H), 7.28 (d, 1H), 7.25 (d, 1H), 7.19 (t, 1H), 6.99 (d, 2H), 6.80 (t, 1H, 6.78 (d, 1H), 6.72 (t, 1H), 4.38 (t, 2H), 3.55 (t, 2H), 3.04 (q, 2H), 1.46 (t, 3H).

EXAMPLE 11

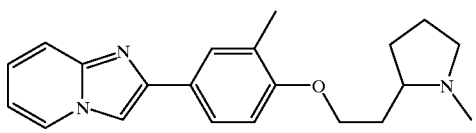

2-[4-[2-(1-Methyl)-2-pyrrolidino]ethoxy-3-methylphenyl]imidazo[1,2-a]pyridine $K_i$=7 nM The title compound was obtained (78 mg) by the same general method as Example 10, by substituting 4-hydroxy-3-methylacetophenone for 4-hydroxyacetophenone and 2-ethoxy-1-methylpyrrolidine for 2-(N-ethylanilino) ethanol. MS (ESI) m/z 336 (MH$^+$); $^1$H-NMR (CDCl$_3$) δ 8.02 (d, 1H), 7.69 (s, 1H), 7.68 (d, 1H), 7.64 (dd, 1H), 7.52, (d, 1H), 7.06 (dd, 1H), 6.80 (d, 1H), 6.66 (t, 1H), 3.98 (m, 2H), 3.49 (dt, 1H), 3.00 (m, 2H), 2.28 (s, 3H), 2.20 (s, 3H), 2.0 –1.5 (m, 6H).

EXAMPLE 12

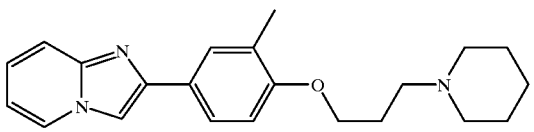

2-(4-Piperidinopropoxy-3-methylphenyl)imidazo[1,2-a]pyridine $K_i$=21 nM

The title compound was obtained (28 mg) by the same general method as Example 10, by substituting 4-hydroxy-3-methylacetophenone for 4-hydroxyacetophenone and 1-propoxypiperidine for 2-(N-ethylanilino)ethanol. MS (ESI) m/z 350 (MH$^+$); $^1$H-NMR (CDCl$_3$) δ 8.11 (d, 1H), 7.79 (s, 1H), 7.76 (s, 1H), 7.73 (d, 1H), 7.62 (d, 1H), 7.15 (dd, 1H), 6.89 (d, 1H), 6.77 (t, 1H), 4.06 (t, 2H), 2.45 (m, 6H), 2.29 (s, 3H), 1.62 (m, 6H), 1.45 (m, 2H).

EXAMPLE 13

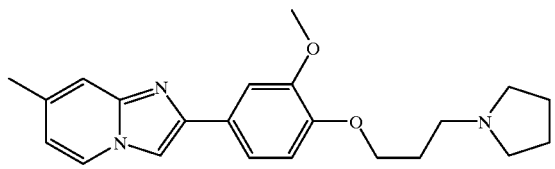

2-[3-Methoxy-4-(3-pyrrolidin-1-yl-propoxy)-phenyl]-7-methyl-imidazo[1,2-a]pyridine $K_i$=63 nM The product of Example 26 Step C (112 mg) and pyrrolidine (1.1 mL) were heated at 85° C. for 3 hours. The reaction was cooled to ambient temperature and partitioned between ethyl acetate (10 mL) and saturated sodium bicarbonate solution (10 mL). The aqueous portion was extracted twice with additional ethyl acetate (10 mL) and once with dichloromethane (10 mL). The organic portions were combined and washed with brine and evaporated. The residue was purified via silica gel chromatography (dichloromethane/ 2M ammonia in methanol) to give the title compound (80 mg). $^1$H-NMR (CDCl$_3$) δ 7.98 (d, J=7.0 Hz, 1H), 7.73 (s, 1H), 7.56 (d, J=2.0 Hz, 1H), 7.42 (dd, J=8.0 Hz, J=2.0 Hz, 1H), 7.38 (br s, 1H), 6.96 (d, J=8.0 Hz, 1H), 6.60 (dd, J=7.0 Hz, J=1.5 Hz, 1H), 4.15 (t, J=7.0 Hz, 2H), 3.99 (s, 3H), 2.67 (t, J=7.5 Hz, 2H), 2.55 (m, 4H), 2.40 (s, 3H), 2.12 (m, 2H), 1.80 (m, 4H).

EXAMPLE 14

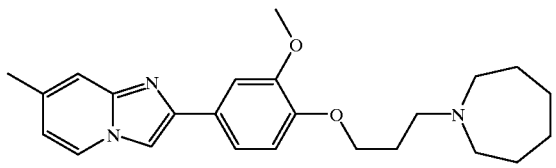

2-[4-(3-Azepan-1-yl-propoxy)-3-methoxy-phenyl]-7-methyl-imidazo[1,2-a]pyridine $K_i$=34 nM The product of Example 26 Step C (130 mg) and hexamethyleneimine (1.5 mL) were heated at 100° C. for 1.5 hours. The reaction was cooled to ambient temperature and partitioned between ethyl acetate (10 mL) and saturated sodium bicarbonate solution (10 mL). The aqueous portion was extracted twice with additional ethyl acetate (10 mL) and once with dichloromethane (10 mL). The organic portions were combined and washed with brine and evaporated. The residue was purified via silica gel chromatography (dichloromethane/2M ammonia in methanol) to give the title compound (57 mg). $^1$H-NMR (CD$_3$OD) δ8.18 (d, J=7.0 Hz, 1H), 7.94 (s, 1H), 7.51 (d, J=2.0 Hz, 1H), 7.38 (dd, J=8.0 Hz, J=2.0 Hz, 1H), 7.27 (s, 1H), 6.94 (d, J=8.0 Hz, 1H), 6.70 (dd, J=7.0 Hz, J=1.5 Hz, 1H), 4.01 (t, J=6.0 Hz, 2H), 3.91 (s, 3H), 2.70 (m, 6H), 2.38 (s, 3H), 1.97 (m, 2H), 1.63 (m, 8H)

EXAMPLE 15

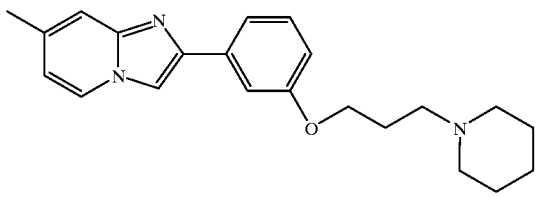

7-Methyl-2-[3-(3-piperidin-1-yl-propoxy)-phenyl]-imidazo[1,2-a]pyridine K$_i$=28 nM Step A Preparation 1-[3-(3-Chloro-propoxy)-phenyl]-ethanone A mixture of 3'-hydroxyacetophenone (5 g) and 1-bromo-3-chloropropane (5.0 mL) in acetone (40 mL) was treated with potassium carbonate (8.1 g). The mixture was stirred at reflux temperature for 17 hours. The reaction was cooled to ambient temperature and filtered. The filtrate was concentrated in vacuo. The residue was partitioned between dichloromethane (50 mL) and H$_2$O (50 mL). The aqueous phase was washed with two fresh portions of dichloromethane. The combined organic phases were washed with brine, dried over magnesium sulfate, filtered and evaporated to yield the title compound (8.6 g) which was used without further purification.

Step B Preparation of 2-Bromo-1-[3-(3-chloro-propoxy)-phenyl]-ethanone

A solution of the product of Step A (2.1 g) in ether (11 mL) was treated with bromine (0.53 mL) and the mixture stirred for 26 hours. The mixture was poured into saturated sodium bicarbonate solution (50 mL) and the organic layer was separated. The aqueous layer was washed with a fresh portion of ether (50 mL) and the combined organic layers were washed with brine (50 mL), dried over magnesium sulfate, filtered, and evaporated to yield the title compound (2.8 g).

Step C Preparation of 2-[3-(3-Chloro-propoxy)-phenyl]-7-methyl-imidazo[1,2-a]pyridine A solution of the product of Step B (2.6 g) and 2-amino-4-picoline (0.96 g) in ethanol (10 mL) was heated at 73° C. for 2 hours. The reaction mixture was cooled to ambient temperature and the solvent evaporated in vacuo. The residue was dissolved in dichloromethane (75 mL), washed with saturated sodium bicarbonate solution (2×75 mL), brine (75 mL), dried over magnesium sulfate, filtered and evaporated. The residue was purified via silica gel chromatography (ethyl acetate/hexane) to give the title compound (1.3 g).

Step D 7-Methyl-2-[3-(3-piperidin-1-yl-propoxy)-phenyl]-imidazo[1,2-a]pyridine

The product of Step C (271 mg) and piperidine (2.0 mL) were heated at 100° C. for 2 hours. The reaction was cooled to ambient temperature and partitioned between ethyl acetate (10 mL) and saturated sodium bicarbonate solution (10 mL). The aqueous portion was extracted with a fresh portion of ethyl acetate (10 mL) and the organic portions combined and washed with brine (10 mL). The organic portions were dried over magnesium sulfate, filtered and evaporated. The residue was purified via silica gel chromatography (dichloromethane/methanol) to give the title compound (193 mg). $^1$H-NMR (CD$_3$OD) δ 8.27 (d, J=7.0 Hz, 1H), 8.08 (s, 1H), 7.46 (m, 2H), 7.31 (m, 2H), 6.88 (m, 1H), 6.76 (m, 1H), 4.09 (t, J=6.0 Hz, 2H), 2.58 (m, 6H), 2.42 (s, 3H), 2.04 (m, 2H), 1.65 (m, 4H), 1.51 (m, 2H).

EXAMPLE 16

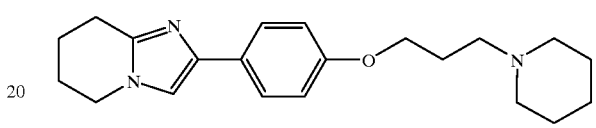

2-[4-(3-Piperidin-1-yl-propoxy)-phenyl]-5,6,7,8-tetrahydro-imidazo[1,2-a]pyridine K$_i$=0.75 nM Step A Preparation of 2-[4-(3-Chloro-propoxy)-phenyl]-imidazo[1,2-a]pyridine A solution of the product of Example 8 Step B (402 mg) and 2-aminopyridine (130 mg) in EtOH (2 mL) was heated at 73° C. for 2.5 hours. The reaction mixture was cooled to ambient temperature and the solvent evaporated in vacuo. The residue was dissolved in dichloromethane (15 mL), washed with saturated sodium bicarbonate solution (2×15 mL), brine (15 mL), dried over magnesium sulfate, filtered and evaporated. The residue was purified via silica gel chromatography (ethyl acetate/hexanes) to give the title compound (235 mg).

Step B Preparation of 2-[4-(3-Chloro-propoxy)-phenyl]-5,6,7,8-tetrahydro-imidazo[1,2-a]pyridine To a Parr bottle charged with a mixture of platinum (IV) oxide (30 mg) in ethanol (3 mL) was added a solution of the product of Step A (90 mg) in methanol (6 ml). The mixture was hydrogenated at 40 psi for 4 hours and filtered through a Celite pad which was rinsed with several additional milliliters of methanol and ethanol. The filtrate was collected and evaporated in vacuo to yield the title compound (88 mg) which was used without further purification.

Step C Preparation of 2-[4-(3-Piperidin-1-yl-propoxy)-phenyl]-5,6,7,8-tetrahydro-imidazo[1,2-a]pyridine The product of Step B (83 mg) and piperidine (1.0 mL) were heated at 100° C. for 1.5 hours. The reaction was cooled to ambient temperature and partitioned between ethyl acetate (10 mL) and saturated sodium bicarbonate solution (10 mL). The aqueous portion was extracted with a fresh portion of ethyl acetate (2×10 mL) and the organic portions combined and washed with brine (10 mL). The organic portions were dried over magnesium sulfate, filtered and evaporated. The residue was purified via silica gel chromatography (dichloromethane/methanol) to give the title compound (35 mg). $^1$H-NMR (CDCl$_3$) δ 7.61 (m, 2H), 7.16 (s, 1H), 6.92 (m, 2H), 4.01 (m, 4H), 2.84 (t, J=6.0 Hz, 2H), 2.72 (m, 6H), 2.00 (m, 6H), 1.68 (m, 4H), 1.56 (m, 2H).

EXAMPLE 17

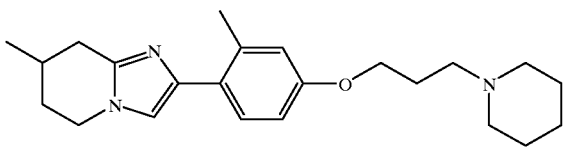

7-Methyl-2-[2-methyl-4-(3-piperidin-1-yl-propoxy)-phenyl]-5,6,7,8-tetrahydro-imidazo[1,2-a]pyridine $K_i$=3.2 nM Step A Preparation of 2-[4-(3-Chloro-propoxy)-2-methyl-phenyl]-7-methyl-5,6,7,8-tetrahydro-imidazo[1,2-a]pyridine To a Parr bottle charged with a mixture of platinum (IV) oxide (35 mg) in ethanol (3 mL) was added a solution of the product of Example 22 Step C (104 mg) in methanol (7 ml). The mixture was hydrogenated at 45 psi for 3 hours and filtered through a Celite pad which was rinsed with several additional milliliters of methanol and ethanol. The filtrate was collected and evaporated in vacuo to yield a residue which was purified via silica gel chromatography (dichloromethane/methanol) to give the title compound (50 mg).

Step B Preparation of 7-Methyl-2-[2-methyl-4-(3-piperidin-1-yl-propoxy)-phenyl]-5,6,7,8-tetrahydro-imidazo[1,2-a]pyridine The product of Step A (49 mg) and piperidine (1.0 mL) were heated at 100° C. for 2 hours. The reaction was cooled to ambient temperature and partitioned between ethyl acetate (10 mL) and saturated sodium bicarbonate solution (10 mL). The aqueous portion was extracted with a fresh portion of ethyl acetate (2×10 mL) and the organic portions combined and washed with brine (10 mL). The organic portions were dried over magnesium sulfate, filtered and evaporated. The residue was purified via silica gel chromatography (dichloromethane/methanol) to give the title compound (45 mg). $^1$H-NMR (CD$_3$OD) δ 7.47 (d, J=8.4 Hz, 1H), 6.99 (s, 1H), 6.78 (m, 2H), 4.13 (m, 1H), 4.07 (t, J=6.0 Hz, 2H), 3.98 (m, 1H), 2.99 (m, 1H), 2.89 (m, 6H), 2.41 (m, 4H), 2.10 (m, 4H), 1.75 (m, 5H), 1.60 (m, 2H), 1.18 (d, J=6.5 Hz, 3H)

EXAMPLE 18

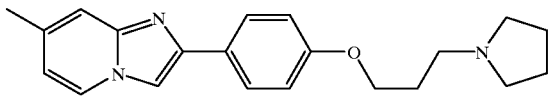

2-(4-Pyrrolidinopropoxyphenyl)-7-methylimidazo[1,2-a]pyridine $K_i$=2 nM

The product of Step C, Example 8 (126 mg) and pyrrolidine (1.5 mL) were heated at 85° C. for 4 hours. The reaction was cooled to ambient temperature and partitioned between ethyl acetate (6 mL) and half-saturated sodium bicarbonate solution (6 mL). The aqueous portion was extracted with additional ethyl acetate (6 mL) and the organic portions combined and evaporated. The residue was purified via silica gel chromatography (dichloromethane/methanol) to give the title compound (50.3 mg). $^1$H-NMR (CD$_3$OD) δ 8.18 (d, 7.0 Hz, 1H), 7.91 (s, 1H), 7.77 (m, 2H), 7.25 (s, 1H), 6.94 (m, 2H), 6.68 (m, 1H), 4.01 (t, J=6.0 Hz, 2H), 2.71 (m, 2H), 2.64 (m, 4H), 2.37 (s, 3H), 2.01 (m, 2H), 1.83 (m, 4H)

EXAMPLE 19

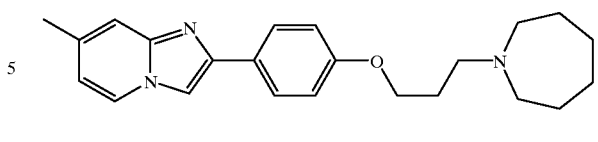

2-(4-hexamethyleneiminopropoxyphenyl)-7-methylimidazo[1,2-a]pyridine $K_i$=2 nM

The product of Step C, Example 8 (100 mg) and hexamethyleneimine (1.5 mL) were heated at 100° C. for 2 hours. The reaction was cooled to ambient temperature and partitioned between ethyl acetate (6 mL) and saturated sodium bicarbonate solution (6 mL). The aqueous portion was extracted with additional ethyl acetate (6 mL). The organic portions were combined, washed with brine and evaporated. The residue was purified via silica gel chromatography (dichloromethane/methanol) to give the title compound (60 mg). $^1$H-NMR (CD$_3$OD) δ 8.15 (d, J=7.0 Hz, 1H), 7.88 (s, 1H), 7.76 (m, 2H), 7.23 (s, 1H), 6.92 (m, 2H), 6.65 (m, 1H), 3.97 (t, J=6.0 Hz, 2H), 2.78 (m, 6H), 2.34 (s, 3H), 1.97 (m, 2H), 1.64 (m, 8H)

EXAMPLE 20

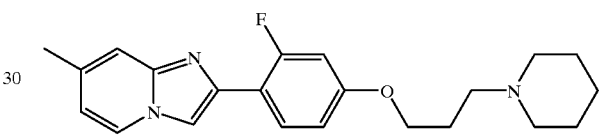

2-(4-Piperidinopropoxy-2-fluorophenyl)-7-methylimidazo[1,2-a]pyridine $K_i$=10 nM Step A Preparation of 2'-fluoro-4'-chloropropoxyacetophenone A mixture of 2'-fluoro-4-hydroxy-acetophenone (5.0 g) and 1-bromo-3-chloropropane (4.5 mL) in acetone (35 mL) was treated with potassium carbonate (7.2 g). The mixture was stirred at 52° C. for approximately 18 hours. The reaction mixture was filtered and the filtrate collected and evaporated. The residue was partitioned between dichloromethane (75 mL) and water (75 mL). The aqueous fraction was washed twice with fresh portions of dichloromethane (75 mL). The organic fractions were combined, washed with brine, and evaporated to give the title compound which was used without further purification.

Step B Preparation of alpha-bromo-2'-fluoro-4'-chloropropoxyacetophenone

A solution of the product of Step A (2.3 g) in ether (10 mL) was treated with bromine (0.51 mL) and the mixture stirred for approximately 17 hours. The mixture was slowly poured into saturated sodium bicarbonate solution (40 mL) and then the organic layer was separated. The aqueous layer was washed with a fresh portion of ether (40 mL). The combined organic layers were washed with a fresh portion of water (50 mL), dried over magnesium sulfate, filtered and evaporated to give the title compound (3.1 g).

Step C Preparation of 2-(4'-chloropropoxy-2'fluorophenyl)-7-methylimidazo[1,2-a]pyridine A solution of the product of Step B (1.0 g) and 2-amino-4-picoline (0.357 g) in ethanol (4 mL) was heated at 73° C. for 18 hours. The reaction mixture was cooled to ambient temperature and the solvent evaporated in vacuo. A portion of the residue was purified via silica gel chromatography (ethyl acetate/hexane) directly. The remainder of the residue was dissolved in methanol/dichloromethane and treated with Dowex® 550A basic resin (Aldrich, Milwaukee, Wis.) for 10 minutes. The resin was removed via filtration and the filtrate evaporated prior to silica gel chromatography (ethyl acetate/hexane). The combined material (0.42 g) containing the title compound was used without further purification.

Step D Preparation of 2-(4'-piperidinopropoxy-2'fluorophenyl)-7-methylimidazo[1,2-a]pyridine The product of Step C (118 mg) and piperidine (1.5 mL) were heated at 100° C. for 2.5 hours. The reaction was cooled to ambient temperature and partitioned between ethyl acetate (10 mL) and saturated sodium bicarbonate solution (10 mL). The aqueous portion was extracted with additional ethyl acetate (10 mL) and the organic portions combined and evaporated. The residue was purified via silica gel chromatography (dichloromethane/methanol) to give the title compound (130 mg). $^1$H-NMR (CD$_3$OD) δ 8.22 (d, J=8.0 Hz, 1H), 7.98 (m, 2H), 7.27 (s, 1H), 6.76 (m, 3H), 4.00 (t, J=6.0 Hz, 2H), 2.48 (m, 6H), 2.38 (s, 3H), 1.96 (m, 2H), 1.61 (m, 4H), 1.47 (m, 2H)

EXAMPLE 21

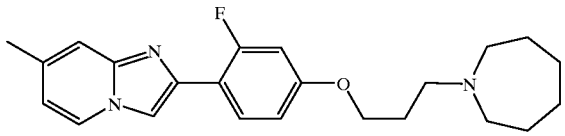

2-(4-hexamethyleneiminopropoxy-2-fluorophenyl)-7-methylimidazo[1,2-a]pyridine $K_i$=15 nM The product of Step C, Example 20 (56 mg) and hexamethyleneimine (1.0 mL) were heated at 100° C. for 2 hours. The reaction was cooled to ambient temperature and partitioned between ethyl acetate (10 mL) and saturated sodium bicarbonate solution (10 mL). The aqueous portion was extracted with additional ethyl acetate (10 mL). The organic portions were combined and evaporated. The residue was purified via silica gel chromatography (dichloromethane/methanol) to give the title compound (40 mg). $^1$H-NMR (CD$_3$OD) δ 8.23 (d, J=7.0 Hz, 1H), 7.98 (m, 2H), 7.27 (s, 1H), 6.76 (m, 3H), 4.01 (t, J=6.0 Hz, 2H), 2.66 (m, 6H), 2.38 (s, 3H), 1.94 (m, 2H), 1.64 (m, 8H)

EXAMPLE 22

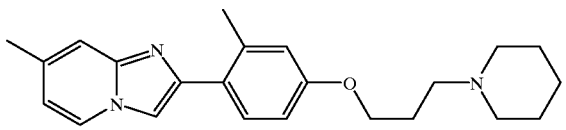

2-(4-Piperidinopropoxy-2-methylphenyl)-7-methylimidazo[1,2-a]pyridine $K_i$=1 nM Step A Preparation of 2'-methyl-4'-chloropropoxyacetophenone A mixture of 4'-hydroxy-2'-methyl-acetophenone (10.5 g) and 1-bromo-3-chloropropane (7.6 mL) in acetone (70 mL) was treated with potassium carbonate (14.5 g). The mixture was stirred at 50° C. for approximately 18 hours. The reaction mixture was cooled to ambient temperature and partitioned between dichloromethane (200 mL) and water (200 mL). The aqueous layer was washed twice with fresh portions of dichloromethane (200 mL) and brine was used to break any emulsions. The organic fractions were combined, dried over sodium sulfate, and evaporated. The residue was re-dissolved in dichloromethane (100 mL) and washed with 0.5 M sodium hydroxide (100 mL) and brine (100 mL), dried over magnesium sulfate, filtered and evaporated to give the title compound which was used without further purification.

Step B Preparation of alpha-bromo-2'-methyl-4'-chloropropoxyacetophenone

A solution of the product of Step A (9.33 g) in ether (42 mL) was treated with bromine (2.1 mL) and the mixture stirred for approximately 17 hours. The mixture was slowly poured into saturated sodium bicarbonate solution (100 mL) and then the organic layer was separated. The aqueous layer was washed with a fresh portion of ether (100 mL). The combined organic layers were washed with a fresh portion of water (100 mL), dried over magnesium sulfate, filtered and evaporated to give the title compound (11 g).

Step C 2-(4'-chloropropoxy-2'-methylphenyl)-7-methylimidazo[1,2-a]pyridine

A solution of the product of Step B (6.77 g) and 2-amino-4-picoline (2.4 g) in ethanol (22 mL) was heated at 72° C. for 10 hours. The reaction mixture was cooled to ambient temperature and dissolved in methanol/dichloromethane and treated with Dowex® 550A basic resin until the pH of the mixture was 7. The resin was removed via filtration and the filtrate evaporated. The title compound was precipitated from ethyl acetate upon addition of hexanes and used without further purification.

Step D Preparation of 2-(4'-piperidinopropoxy-2'-methylphenyl)-7-methylimidazo[1,2-a]pyridine The product of Step C (200 mg) and piperidine (2.0 mL) were heated at 100° C. for 2.5 hours. The reaction was cooled to ambient temperature and partitioned between ethyl acetate (10 mL) and saturated sodium bicarbonate solution (10 mL). The aqueous portion was extracted with additional ethyl acetate (10 mL) and the organic portions combined, washed with brine, and evaporated. The residue was purified via silica gel chromatography (dichloromethane/methanol) to give the title compound (110 mg). $^1$H-NMR (CD$_3$OD) δ 8.28 (d, J=7.0 Hz, 1H), 7.78 (s, 1H), 7.61 (d, J=8.0 Hz, 1H), 7.31 (s, 1H), 6.84 (s, 1H), 6.79 (m, 2H), 4.04 (t, J=6.0 Hz, 2H), 2.50 (m, 12H), 1.99 (m, 2H), 1.64 (m, 4H), 1.51 (m, 2H)

EXAMPLE 23

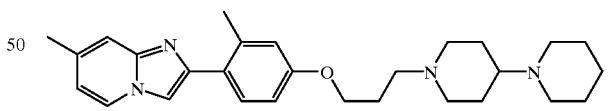

2-(4-(4-Piperidino)piperidinopropoxy-2-methylphenyl)-7-methylimidazo[1,2-a]pyridine $K_i$=14 nM A mixture of the product of Step C, Example 22 (360 mg) and 4-piperidinopiperidine (195 mg) in acetone (5.5 mL) was treated with potassium carbonate (165 mg). The mixture was stirred at 55° C. overnight and evaporated. The residue was partitioned between ethyl acetate (25 mL) and saturated sodium bicarbonate solution (25 mL). The aqueous portion was extracted with additional ethyl acetate (25 mL) and dichloromethane (25 mL) and the organic portions combined, washed with brine, and evaporated. The residue was purified via silica gel chromatography (dichloromethane/2M ammonia in methanol) to give the title compound (150 mg). $^1$H-NMR (CD$_3$OD) δ 8.21 (d, J=7.0 Hz, 1H), 7.75 (s, 1H), 7.68 (m, 1H), 7.29 (s, 1H), 6.80 (m, 2H), 6.68 (m, 1H), 3.95 (t, J=6.0 Hz, 2H), 2.94 (m, 2H), 2.44 (m, 9H), 2.37 (s, 3H), 2.14 (m, 1H), 1.84 (m, 6H), 1.50 (m, 8H).

EXAMPLE 24

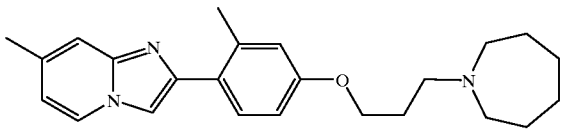

2-(4-hexamethyleneiminopropoxy-2-methylphenyl)-7-methylimidazo[1,2-a]pyridine K$_i$=0.5 nM The product of Step C, Example 22 (300 mg) and hexamethyleneimine (2.0 mL) were heated at 100° C. for 1.0 hour. The reaction was cooled to ambient temperature and partitioned between ethyl acetate (10 mL) and saturated sodium bicarbonate solution (10 mL). The aqueous portion was extracted twice with additional ethyl acetate (10 mL) and the organic portions combined, washed with brine, and evaporated. The residue was purified via silica gel chromatography (dichloromethane/methanol) to give the title compound (70 mg). $^1$H-NMR (CDCl$_3$) δ 7.98 (d, J=7.0 Hz, 1H), 7.83 (d, J=8.4 Hz, 1H), 7.54 (s, 1H), 7.37 (s, 1H), 6.83 (m, 2H), 6.58 (dd, J=7.0 Hz, J=1.5 Hz, 1H), 4.05 (t, J=6.5 Hz, 2H), 2.67 (m, 6H), 2.52 (s, 3H), 2.39 (s, 3H), 1.95 (m, 2H), 1.63 (m, 8H)

EXAMPLE 25

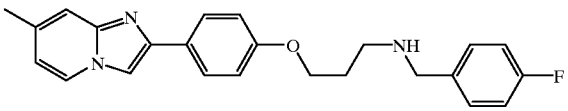

2-(4-(4-Fluorobenzyl)aminopropoxyphenyl)-7-methylimidazo[1,2-a]pyridine K$_i$=1500 nM, MS= 390.1 (M+H)

The product of Step C, Example 8 (160 mg) and 4-fluorobenzylamine (1.0 mL) were heated at 100° C. for 40 minutes. The reaction was cooled to ambient temperature and purified via silica gel chromatography (methanol/dichloromethane) to yield the title compound (16 mg) in approximately 80% purity. $^1$HNMR (CDCl$_3$): δ 7.97 (d, J=7.0 Hz, 1H), 7.85 (m, 2H), 7.69 (s, 1H), 7.36 (br s, 1H), 7.28 (m, 2H), 6.96 (m, 4H), 6.59 (dd, J=7.0 Hz, J=1.5 Hz, 1H), 4.09 (t, J=6.0 Hz, 2H), 3.78 (s, 2H), 2.83 (t, J=7.0 Hz, 2H), 2.39 (s, 3H), 2.00 (m, 2H).

EXAMPLE 26

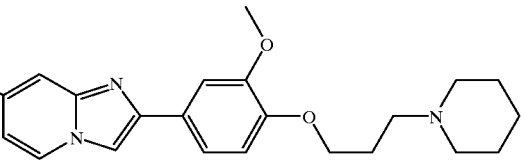

2-(4-Piperidinopropoxy-3-methoxyphenyl)-7-methylimidazo[1,2-a]pyridine K$_i$=159 nM Step A 3'-methoxy-4'-chloropropoxyacetophenone A mixture of acetovanillone (10.0 g) and 1-bromo-3-chloropropane (8.3 mL) in acetone (65 mL) was treated with potassium carbonate (13.3 g). The mixture was stirred at 52° C. for approximately 18 hours. The reaction mixture was cooled to ambient temperature and filtered. The filtrate was evaporated and the residue partitioned between dichloromethane (~100 mL) and water (~100 mL). The aqueous layer was washed (2×) with a fresh portion of dichloromethane. The combined organic layers were washed with brine and evaporated to give the title compound which was used without further purification.

Step B Preparation of alpha-bromo-3'-methoxy-4'-chloropropoxyacetophenone

A solution of the product of Step A (5.9 g) in ether (95 mL) was treated with bromine (1.3 mL) and the mixture stirred for approximately 60 hours. The reaction mixture was slowly poured into saturated sodium bicarbonate (100 mL) and then the organic layer was separated. The aqueous layer was washed with a fresh portion of ether (100 mL). The combined ether layers were washed with water (100 mL), dried over magnesium sulfate, filtered and evaporated. The residue was purified via silica gel chromatography (hexanes/ethyl acetate) to yield the title compound (2.4 g).

Step C Preparation of 2-(4'-chloropropoxy-3'-methoxyphenyl)-7-methylimidazo[1,2-a]pyridine hydrobromide A solution of the product of Step B (1.44 g) and 2-amino-4-picoline (0.486 g) in ethanol (6 mL) was heated at 73° C. for 1 hour. The reaction mixture was cooled to ambient temperature and evaporated to a yellow solid. The solid was stirred with 25 mL of dichloromethane for approximately 10 minutes. The mixture was filtered and the solid product collected to yield the title compound (1.3 g).

Step D Preparation of 2-(4'-piperidinopropoxy-3'-methoxyphenyl)-7-methylimidazo[1,2-a]pyridine The product of Step C (184 mg) and piperidine (1.5 mL) were heated at 100° C. for 4 hours. The reaction was cooled to ambient temperature and partitioned between ethyl acetate (10 mL) and saturated sodium bicarbonate solution (10 mL). The aqueous portion was extracted twice with additional ethyl acetate (10 mL) and once with dichloromethane (10 mL). The organic portions were combined, washed with brine, and evaporated. The residue was purified via silica gel chromatography (dichloromethane/2M ammonia in methanol) to give the title compound (150 mg). $^1$H-NMR (CD$_3$OD) δ 8.17 (d, J=7.0 Hz, 1H), 7.93 (s, 1H), 7.50 (d, J=2.0 Hz, 1H), 7.38 (dd, J=8.0 Hz, J=2.0 Hz, 1H), 7.26 (s, 1H), 6.93 (d, J=8.0 Hz, 1H), 6.68 (dd, J=7.0 Hz, J=1.5 Hz, 1H), 4.00 (t, J=6.0 Hz, 2H), 3.91 (s, 3H), 2.56 (m, 3H), 2.48 (br. s, 3H), 2.38 (s, 3H), 1.98 (m, 2H), 1.60 (m, 4H), 1.47 (m, 2H)

EXAMPLE 27

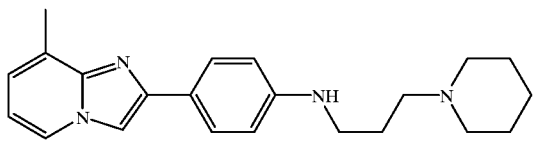

2-[4-[3-(Piperidino)propylamino]phenyl]-8-methylimidazo[1,2-a]pyridine $K_i$=7 nM Step A Preparation of 2-(4'-nitrophenyl)-8-methylimidazo[1,2-a]pyridine A mixture of 2-bromo-4'-nitroacetopheone (4.27 g) and 2-amino-3-picoline (1.9 g) in ethanol (20 mL) was stirred at reflux temperature for 1.5 hours. The reaction mixture was cooled to ambient temperature and filtered. The solid was collected and recrystallized (ethyl acetate/methanol) to yield the title compound (2.2 g).

Step B Preparation of 2-(4'-aminophenyl)-8-methylimidazo[1,2-a]pyridine

A mixture of the product of Step A (1.48 g) and 1,4-cyclohexadiene (6.2 mL) and palladium (10% wt on activated carbon) (1.4 g) in ethanol (100 mL) was stirred at reflux temperature for 2 hours and cooled to ambient temperature and stirred for 12 hours. The reaction mixture was filtered through a pad of celite and the celite pad rinsed with ethanol (100 mL) and methanol (100 mL). The filtrate was collected and evaporated to yield the title compound (710 mg).

Step C Preparation of 2-[4'-[3-(Piperidinyl)]propanamidophenyl]-8-methylimidazo[1,2-a]pyridine To a mixture of the product of Step B (330 mg) and N,N-diisopropylethylamine (0.28 mL) in dichloromethane (3 mL) and N,N-dimethylformamide(1 mL), was added 1-piperidinepropionic acid (256 mg), WSC.HCl (1-Ethyl-3-(3'dimethylaminopropyl)-carbodiimide.HCl) (312 mg), and 1-hydroxybenzotriazole hydrate (220 mg). The solution was stirred at ambient temperature for approximately 18 hours. The mixture was poured into a separatory funnel and washed sequentially with an equal volume of 1 N sodium hydroxide and water. The organic phase was dried over sodium sulfate, decanted and evaporated. The residue was purified via silica gel chromatography (methanol/dichloromethane) to yield the title compound (128 mg).

Step D Preparation of 2-[4'-[3-(Pyrrolidino)propylamino]phenyl]-8-methylimidazo[1,2-a]pyridine A mixture of the product of Step C (122 mg) and borane-methylsulfide complex (0.5 mL of a 2M solution in toluene) in toluene (3.5 mL) was stirred and heated at reflux for 18 hours. The mixture was cooled to ambient temperature and evaporated. The residue was treated with 1 M HCl (10 mL) and heated to reflux. The aqueous mixture was cooled to ambient temperature and treated with solid sodium hydroxide until the pH of the mixture was 8. The aqueous mixture was extracted three times with dichloromethane (10 mL each). The combined organic layers were dried over sodium sulfate, decanted and evaporated. The residue was purified via silica gel chromatography (methanol/dichloromethane) to yield the title compound (60 mg). $^1$H-NMR (CD$_3$OD) δ 8.16 (d, J=7.0 Hz, 1H), 7.90 (s, 1H), 7.72 (m, 2H), 7.00 (m, 1H), 6.71 (m, 3H), 3.16 (t, J=7.0 Hz, 2H), 2.59 (m, 9H), 1.86 (m, 2H), 1.65 (m, 4H), 1.50 (m, 2H)

EXAMPLE 28

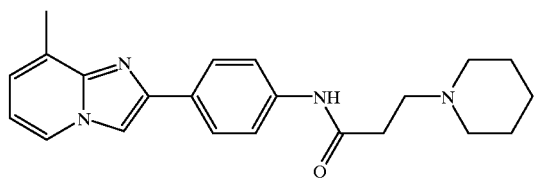

2-[4-[3-(Piperidinyl)]propanamidophenyl]-8-methylimidazo[1,2-a]pyridine $K_i$=158 nM This compound was prepared according to the procedures described Steps A–C, Example 27. $^1$H NMR (CDCl$_3$) δ 7.98 (d, J=7.0 Hz, 1H), 7.92 (m, 2H), 7.80 (s, 1H), 7.62 (m, 2H), 6.93 (m, 1H), 6.67 (t, J=7.0 Hz, 1H), 2.71 (m, 3H), 2.65 (s, 3H), 2.57 (m, 5H), 1.75–1.50 (broad m, 6H)

EXAMPLE 29

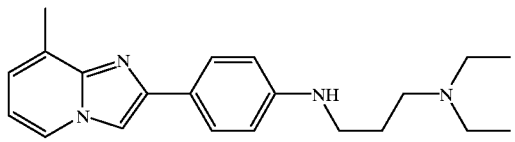

N,N-Diethyl-N'-[4-(8-methyl-imidazo[1,2-a]pyridin-2-yl)-phenyl]-propane-1,3-diamine $K_i$=9 nM The title compound was prepared according to the procedure of Example 27, Step D from the corresponding amide (Example 6). $^1$H NMR (400 MHz, CD$_3$OD) for HCl salt δ 8.59 (d, J=6.5 Hz, 1H), 8.34 (s, 1H), 7.75 (d, J=8.5 Hz, 2H), 7.71 (d, J=7.3 Hz, 1H), 7.37 (t, J=6.9 Hz, 1H), 6.91 (d, J=8.5 Hz, 2H), 3.36 (m, 2H), 3.26 (m, 6H), 2.70 (s, 3H), 2.08 (m, 2H), 1.35 (t, J=7.3 Hz, 6H). MH$^+$=337.2

EXAMPLE 30

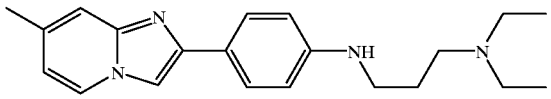

N,N-Diethyl-N'-[4-(7-methyl-imidazol[1,2-a]pyridin-2-yl)-phenyl]-propane-1,3-diamine $K_i$=3 nM The title compound was prepared according to the procedure of Example 27, Step D from the corresponding amide. $^1$H NMR (400 MHz, CD$_3$OD) for HCl salt δ 8.61 (d, J=6.9 Hz, 1H), 8.33 (s, 1H), 7.70 (d, J=8.7 Hz, 2H), 7.63 (s, 1H), 7.32 (dd, J=6.9 and 1.4 Hz, 1H), 6.94 (d, J=8.7 Hz, 2H), 3.36 (m, 2H), 3.26 (q, J=7.3 Hz, 6H), 2.60 (s, 3H), 2.08 (m, 2H), 1.32 (t, J=7.3 Hz, 6H). MH$^+$=337.2.

EXAMPLE 31

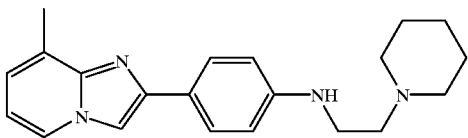

[4-(8-Methyl-imidazo[1,2-a]pyridin-2-yl)-phenyl]-(2-piperidin-1-yl-ethyl)-amine $K_i$=8 nM The title compound was prepared according to the procedure of Example 27, Step D from the corresponding amide (Example 28). $^1$H NMR (400 MHz, CD$_3$OD) for HCl salt δ 8.58 (d, J=6.7 Hz, 1H), 8.33 (d, J=2.4 Hz, 1H), 7.75 (d, J=8.7 Hz, 2H), 7.72 (d, J=7.3 Hz, 1H), 7.37 (t, J=7.0 Hz, 1H), 6.90 (d, J=8.8 Hz, 2H), 3.64 (m, 4H), 3.36 (t, J=6.3 Hz, 2H), 3.03 (dt, J=2.9 and 12.3 Hz, 2H), 2.70 (s, 3H), 1.90 (m, 6H). MH$^+$=335.1

EXAMPLE 32

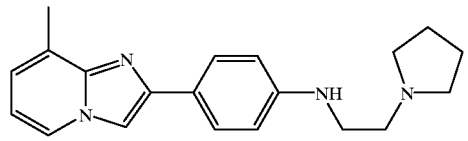

[4-(8-Methyl-imidazo[1,2-a]pyridin-2-yl)-phenyl]-(2-pyrrolidin-1-yl-ethyl)-amine $K_i$=7 nM The title compound was prepared according to the procedure of Example 27, Step D from the corresponding amide (Example 4). $^1$H NMR (400 MHz, CD$_3$OD) for HCl salt δ 8.58 (d, J=6.7 Hz, 1H), 8.33 (d, J=5.6 Hz, 1H), 7.76 (d, J=8.7 Hz, 2H), 7.72 (d, J=7.3 Hz, 1H), 7.37 (t, J=7.0 Hz, 1H), 6.91 (d, J=8.7 Hz, 2H), 3.72 (m, 2H), 3.63 (t, J=6.0 Hz, 2H), 3.47 (t, J=6.0 Hz, 2H), 3.17 (m, 2H), 2.70 (s, 3H), 2.18 (m, 2H), 2.05 (m, 2H). MH$^+$=321.

EXAMPLE 33

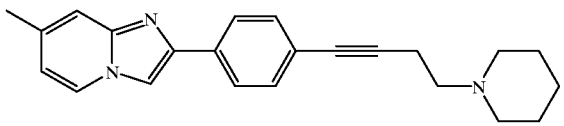

2-[4-[4-Piperidinobut-1-ynyl]phenyl]-7-methylimidazo[1,2-a]pyridine $K_i$=3 nM

Step A Preparation of 2-[4-Bromophenyl]-7-methylimidazo[1,2-a]pyridine

A mixture of 2,4'-dibromoacetophenone (22.4 g) and 2-amino-4-picoline (8.68 g) in ethanol (80 mL) was heated at reflux temperature for 3 hours. The reaction mixture was cooled to ambient temperature and the crystalline solid isolated by filtration, washed with ethanol and dried in vacuo to give the title compound (13.1 g).

Step B Preparation of 2-[4-[4-Hydroxybut-1-ynyl]phenyl]-7-methylimidazo[1,2-a]pyridine The product of Step A (1.8 g) in dry acetonitrile (40 mL) was treated sequentially with tetrakis(triphenylphosphine) palladium(O) (0.1 g), triethylamine (1.27 g), and CuI (10 mg) then heated at 60° C. for 30 minutes. The mixture was cooled to ambient temperature, treated with 3-butyn-1-ol (0.361 g) and heated at reflux temperature for 18 hours. The mixture was cooled to ambient temperature and evaporated to dryness. The residue was crystallized, twice, from acetone to afford the title compound (1.02 g).

Step C Preparation of 2-[4-[4-Methanesulfonyloxybut-1-ynyl]phenyl]-7-methylimidazo[1,2-a]pyridine The product of Step B (0.135 g) in dichloromethane (3 mL) was treated with pyridine (0.37 g) and cooled to 10° C. The cold solution was treated with methanesulfonyl chloride (0.112 g) and allowed to stir and warm to ambient temperature over 18 hours. The reaction mixture was washed with 1% H$_2$SO$_4$ solution, saturated sodium bicarbonate solution, dried over magnesium sulfate, filtered and evaporated to give the title compound (0.115 g).

Step D Preparation of 2-[4-[4-Piperidinobut-1-ynyl]phenyl]-7-methylimidazo[1,2-a]pyridine The product of Step C (1.00 g) in acetonitrile (15 mL) was treated with piperidine (0.269 g) and potassium carbonate (1.17 g) and heated at reflux for 18 hours. The reaction mixture was cooled to ambient temperature, washed with water (20 mL), dried over magnesium sulfate, filtered and evaporated to give crude product. Silica gel chromatography (methanol/dichloromethane) afforded the title compound (1.0 g). MS (ESI) m/z 344.1 (M+H$^+$). $^1$H NMR (DMSO) δ 8.23 (d, J=6.95 Hz, 1 H), 8.15 (s, 1 H), 7.73 (d, J=8.37 Hz, 2 H), 7.25 (d, J=8.34 Hz, 2 H), 7.17 (s, 1 H), 6.58 (dd, J=6.9,1.45 Hz, 1 H), 2.33 (m, 6 H), 2.23 (b, 2 H), 2.18 (s, 3 H). 1.33 (pent, 4 H), 1.21 (pent, 2 H). HRMS: MH$^+$ calcd for C$_{23}$H$_{26}$N$_3$, 344.2127; found, 344.2134. Analysis: Calc'd for C$_{23}$H$_{25}$N$_3$; C, 80.43; H, 7.34; N, 12.23. Found: C, 80.27; H, 7.15; N, 11.81.

EXAMPLE 34

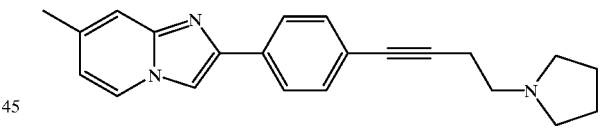

2-[4-[4-Pyrrolidinobut-1-ynyl]phenyl]-7-methylimidazo[1,2-a]pyridine $K_i$=3 nM

The product of Step C, Example 33, (0.09 g) in acetonitrile (5 mL) was treated with pyrrolidine (0.027 g) and potassium carbonate (0.105 g) and heated at reflux for 18 hours. The reaction mixture was cooled to ambient temperature, diluted with ethyl acetate (20 mL), washed with water (20 mL), dried over magnesium sulfate, filtered and evaporated to give crude product. Silica gel chromatography (methanol/dichloromethane) afforded the title compound (0.018 g). MS (ESI) m/z 330.1 (M+H$^+$). $^1$H NMR (CDCl$_3$) δ 7.92 (d, J=6.70 Hz, 1 H), 7.79 (d, J=8.28 Hz, 2 H), 7.71 (s, 1 H), 7.38 (d, J=8.28 Hz, 2 H), 7.30 (s, 1 H), 6.54 (dd, J=6.89, 1.48 Hz, 1 H), 2.72 (m, 2 H), 2.61(m, 6 H), 2.33 (s, 3 H). 1.76 (m, 4 H). HRMS: MH$^+$ calcd for C$_{22}$H$_{24}$N$_3$, 330.1970; found, 330.1976.

EXAMPLE 35

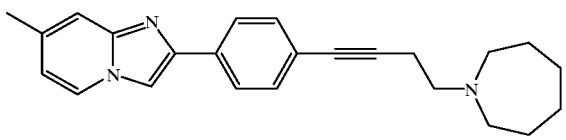

2-[4-[4-hexamethyleneimino-1-ynyl]phenyl]-7-methylimidazo[1,2-a]pyridine $K_i$=50 nM The product of Step C, Example 33, (0.09 g) in acetonitrile (5 mL) was treated with hexamethyleneimino (0.038 g) and potassium carbonate (0.105 g) and heated at reflux for 18 hours. The reaction mixture was cooled to ambient temperature, diluted with ethyl acetate (20 mL), washed with water (20 mL), dried over magnesium sulfate, filtered and evaporated to give crude product. Silica gel chromatography (methanol/dichloromethane) afforded the title compound (0.024 g). MS (ESI) m/z 358.1 (M+H$^+$). $^1$H NMR (CDCl$_3$) δ 7.92 (d, J=6.89 Hz, 1 H), 7.79 (d, J=8.30 Hz, 2 H), 7.70 (s, 1 H), 7.32 (d, J=8.28 Hz, 2 H), 7.30 (s, 1 H), 6.54 (dd, J=6.88, 1.42 Hz, 1 H), 2.81 (m, 2H), 2.70 (mb, 4 H), 2.55 (t, J=7.5 Hz, 2 H). 2.33 (s, 3 H), 1.55 (m, 8H), HRMS: MH$^+$ calcd for $C_{24}H_{28}N_3$, 358.2283; found, 358.2265. Analysis: Calc'd for $C_{24}H_{27}N_3$ 0.6CH$_2$Cl$_2$; C, 71.54; H, 6.90; N, 10.15. Found: C, 71.19; H, 6.76; N, 9.97.

EXAMPLE 36

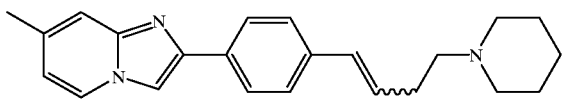

(E/Z)-2-[4-[4-Piperidinobut-1-enyl]phenyl]-7-methylimidazo[1,2-a]pyridine

Step A Preparation of 4-Piperidinylbut-1-ene

4-Bromobut-1-ene (1.35 g) was treated with piperidine (1.7 g) and heated at reflux for 3 hours. The mixture was cooled to ambient temperature, filtered and the residue washed with ether (50 mL). The combined filtrate and washings were evaporated to give the title compound (1.3 g).

Step B (E/Z)-2-[4-[4-Piperidinobut-1-enyl]phenyl]-7-methylimidazo[1,2-a]pyridine The product of Step A (0.76 g) was combined with the product of Example 33, Step A (1.21 g) and treated with triethylamine (74 mL), palladium(II)acetate (0.095 g), triphenylphosphine (0.221 g) and N,N-dimethylformamide (5 mL). The mixture was heated at reflux for 24 hours and cooled to ambient temperature. The reaction mixture was filtered and the residue washed with ethyl acetate (150 mL). The filtrate and washings were combined, washed with water (2×200 mL), dried over sodium sulfate, filtered and evaporated to give crude product. The crude product was purified via silica gel chromatography (ethanol/dichloromethane) to give the title compound (0.8 g). MS (ESI) m/z 346.1 (M+H$^+$). $^1$H NMR (CDCl$_3$) δ 7.91 (d, J=4.4 Hz, 1 H), 7.83–7.77 (m, 2 H). 7.71 and 7.69 (s, 1 H E/Z), 7.34–7.29 (m, 3 H), 6.53–6.51 (m, 1 H), 6.40 (dd, J=16.00, 9.20 Hz, 1 H E/Z), 6.22–6.13 (m, 1 H) 2.44–2.39 (m, 6 H), 2.32 (s, 3 H), 1.80–1.38 (m, 8 H), HRMS: MH$^+$ calcd for $C_{23}H_{28}N_3$, 346.2283; found, 346.2274. Analysis: Calc'd for $C_{23}H_{27}N_3$; C, 79.96; H, 7.88; N, 12.16. Found: C, 79.90; H, 7.77; N, 11.79.

EXAMPLE 37

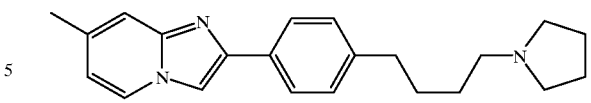

2-[4-[4-Pyrrolidinobutyl]phenyl]-7-methylimidazo[1,2-a]pyridine $K_i$=10 nM

Step A Preparation of 2-[4-[4-Hydroxybutyl]phenyl]-7-methylimidazo[1,2-a]pyridine The product of Step B, Example 33 (0.3 g) in ethanol (15 mL) was hydrogenated over 5% palladium on barium sulfate (0.06 g) for 4.5 hours. The reaction mixture was filtered and evaporated to afford the title compound (0.282 g).

Step B Preparation of 2-[4-[4-Methanesulfonyloxybutyl]phenyl]-7-methylimidazo[1,2-a]pyridine The product of Step A (0.33 g) in dichloromethane (20 mL) was treated with triethylamine (0.36 g) and cooled to 0° C. The cold solution was treated with methanesulfonyl chloride (0.338 g) and allowed to stir and warm to ambient temperature over 18 hours. The reaction mixture was washed with water (50 mL), saturated sodium bicarbonate solution (25 mL), water (50 mL), dried over sodium sulfate, filtered and evaporated to give the crude title compound (0.53 g). The crude product was used, Step C, without further purification.

Step C Preparation of 2-[4-[4-Pyrrolidinobutyl]phenyl]-7-methylimidazo[1,2-a]pyridine The crude product from Step B (0.14 g) in acetonitrile (10 mL) was treated with pyrrolidine (0.056 g) and potassium carbonate (0.162 g) and heated at reflux for 18 hours. The reaction mixture was cooled to ambient temperature, diluted with ethyl acetate (100 mL), washed with water (50 mL), dried over magnesium sulfate, filtered and evaporated to give crude product. Silica gel chromatography (methanol/dichloromethane/ammonia) afforded the title compound (0.054 g). MS (ESI) m/z 334.1 (M+H$^+$). $^1$H NMR (CDCl$_3$) δ 8.13 (d, J=6.93 Hz, 1H), 7.99 (d, J=8.20 Hz, 2H), 7.89 (s, 1H), 7.52 (s, 1H), 7.39 (d, J=8.2 Hz, 2H), 6.74 (dd, J=6.89, 1.57 Hz, 1H), 2.81 (m, 2H), 2.65 (m, 6H). 2.54 (s, 3H), 1.95–1.71 (m, 8H), HRMS: MH$^+$ calcd for $C_{22}H_{28}N_3$, 334.2283; found, 334.2281. Analysis: Calc'd for $C_{22}H_{27}N_3H_2O$; C, 75.18; H, 8.32; N, 11.96. Found: C, 74.90; H, 8.18; N, 11.77.

EXAMPLE 38

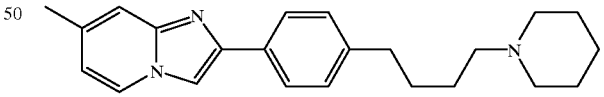

7-Methyl-2-[4-(4-piperdin-1-yl-butyl)-phenyl]imidazo[1,2-a]pyridine $K_i$=29 nM

Step A 2-amino-4-picoline (8.68 g, 80.266 mmol) and 2,4'-dibromoacetophenone (22.4 g, 80.59 mmol) were dissolved into absolute ethanol (80 mL). The resulting solution was allowed to reflux under nitrogen for 3 h. The reaction mixture was cooled and filtered to yield solid crude 16.8 g (72.7%). Crude product was crystallized with boiling ethanol (100 mL) to yield 13.3 g (57.5%) as a pure white crystalline solid.

Step B

A mixture of bromo product from step A (720.4 mg, 2.5 mmol), 3-butyn-1-ol (361 mg, 5 mmol), cuprous iodide (10 mg, 0.052 mmol), triethylamine (1.743 mL, 12.5 mmol), tetrakis (triphenylphosphine)Pd(O) (100 mg, 0.087 mmol) was refluxed in anh. acetonitrile (40 mL) for 18 h. Cooled to room temperature and evaporated to dryness to yield 1.745 g crude yellow solid. The crude was purified by silica-gel column chromatography using 2M ammonia in methanol:dichloromethane (7:93) as a solvent system. The yield of the pure alkyl alcohol was 390 mg (56.5%), a light yellow solid.

Step C

To a solution of alkyl alcohol from step B (300 mg, 1.09 mmol) into ethanol (15 mL) was added 5% Pd/BaSO$_4$ (50 mg). The mixture was hydrogenated at ambient condition for 4½ h. under stirring. Filtered and evaporated to dryness to yield almost pure saturated alcohol (257 mg, 100%).

Step D

To a cooled solution at 5° C. of alcohol from step C (330 mg, 1.18 mmol) and triethylamine (360 mg, 3.54 mmol) in dichloromethane (20 mL) was added slowly methanesulfonyl chloride (338 mg, 3.00 mmol). Reaction mixture was allowed to stir overnight at room temperature under nitrogen atmosphere. Then reaction mixture was diluted to 60 mL with more dichloromethane and washed successively with cold 5% NaHCO$_3$ (aq) (2×25 mL) and cold water (2×20 mL). Organic phase was dried over anhydrous Na$_2$SO$_4$, filtered and evaporated to dryness to yield almost pure mesylate in quantitative yield.

Step E

A mixture of mesylate (140 mg, 0.39 mmol) from step D, piperidine (66.5 mg, 0.78 mmol) and anhydrous K$_2$CO$_3$ (162 mg, 1.17 mmol) in anhydrous acetonitrile (10 mL) was refluxed overnight under nitrogen atmosphere. Then the reaction mixture was cooled to room temperature and partitioned between dichloromethane and water. Separated organic phase was dried over Na$_2$SO$_4$, filtered and evaporated to dryness to yield 233 mg crude product. Crude product was purified on silica gel column using 2M ammonia in methanol:dichloromethane (7:93) as a solvent system to yield 65 mg (48%) final pure product. MS (ESI) m/z 348.1 (M+H$^+$). $^1$H NMR (CDCl$_3$) δ 7.91 (d, J=7.33 Hz, 1 H), 7.77 (d, J=8.59 Hz, 2 H), 7.67 (s, 1 H), 7.30 (s, 1H), 7.16 (d, J=8.08 Hz, 2 H), 6.52 (dd, J=7.07, 2.02 Hz, 1 H), 2.58 (t, J=7.83 Hz, 2 H), 2.28 (m, 8 H), 1.52 (m, 11 H). HRMS: MH$^+$ calcd for C$_{23}$H$_{30}$N$_3$, 348.2440; found, 348.2455. Analysis: Calc'd for C$_{23}$H$_{29}$N$_3$; C, 79.5; H, 8.41; N, 12.09. Found: C, 79.18; H, 8.47; N, 11.90.

EXAMPLE 39

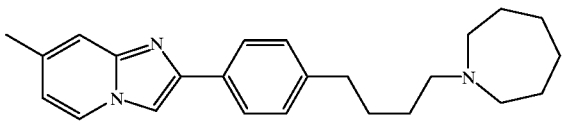

2-[4-(4-Azepan-1-yl-butyl)-phenyl]-7-methyl-imidazo[1,2-a]pyridine K$_i$=57 nM

A mixture of mesylate (Example 1, Step D) (140 mg, 0.39 mmol) from step D, hexamethyleneimine (77.4 mg, 0.78 mmol) and anhydrous K$_2$CO$_3$ (162 mg, 1.17 mmol) in anhydrous acetonitrile (10 mL) was refluxed overnight under nitrogen atmosphere. Then the reaction mixture was cooled to room temperature and partitioned between dichloromethane and water. Separated organic phase was dried over Na$_2$SO$_4$, filtered and evaporated to dryness to yield 190 mg crude product. Crude product was purified on silica gel column using 2M ammonia in methanol:dichloromethane (7:93) as a solvent system to yield 52 mg (37%) final pure product. MS (ESI) m/z 362.3 (M+H). $^1$H NMR (CDCl$_3$) δ 7.89 (d, J=6.84 Hz, 1 H), 7.76 (d, J=8.2 Hz, 2 H), 7.66 (s, 1 H), 7.29 (s, 1 H), 7.15 (d, J=8.16, 2 H), 6.51 (dd, J=6.88, 1.52 Hz, 1 H), 2.59 (m, 6 H), 2.47 (t, J=7.68 Hz, 2 H), 2.32 (s, 3 H), 1.57 (m, 12 H). HRMS: MH$^+$ calcd for C$_{24}$H$_{32}$N$_3$, 362.2596; Found, 362.2589. Analysis: Calc'd for C$_{24}$H$_{31}$N$_3$ 0.25 H$_2$O; C, 78.74; H, 8.56; N, 11.60. Found: C, 78.83; H, 8.59; N, 11.43.

EXAMPLE 40

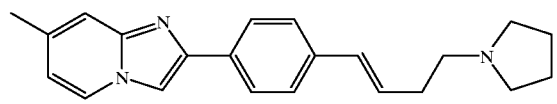

7-Methyl-2-[4-(4-pyrrolidin-1-yl-but-1-enyl)-phenyl]imidazo[1,2-a]pyridine K$_i$=17 nM Step A A mixture of bromo product from Example 38, Step A (2.872 g, 10 mmol), 3-butene-1-ol (0.938 g, 13 mmol), Pd(OAc)$_2$ (224.5 mg, 1 mmol) and triphenylphosphine (525 mg, 2 mmol) was dissolved into triethylamine (12.65 g, 125 mmol) under nitrogen atmosphere and refluxed for 24 h. The reaction mixture was cooled to room temperature and diluted with ethyl acetate (100 mL). The resulting solution was washed with water (2×30 mL). Dried over anhydrous Na$_2$SO$_4$, filtered and evaporated to dryness to yield 2.5 g brownish yellow crude product. Crude product was purified on silica gel column using acetone:dichloromethne (2:8) yielding 0.60 g (18.1%) pure product.

Step B

To a cooled solution at 5° C. of butenol from step B (580 mg, 2.083 mmol) and triethylamine (632.5 mg, 6.25 mmol) in dichloromethane (40 mL) was added slowly methanesulfonyl chloride (716 mg, 6.25 mmol). Reaction mixture was allowed to stir overnight at room temperature under nitrogen atmosphere. Then reaction mixture was diluted to 100 mL with more dichloromethane and washed successively with cold 5% NaHCO$_3$ (aq) (2×30 mL) and cold water (2×30 mL). Organic phase was dried over anhydrous Na$_2$SO$_4$, filtered and evaporated to dryness to yield almost pure mesylate in quantitative yield.

Step C

A mixture of mesylate (120 mg, 0.35 mmol) from step C, pyrrolidine (74.7 mg, 1.05 mmol) and anhydrous K$_2$CO$_3$ (146 mg, 1.05 mmol) in anhydrous acetonitrile (10 mL) was refluxed 3 h. under nitrogen atmosphere. Then the reaction mixture was cooled to room temperature and partitioned between dichloromethane and water. Separated organic phase was dried over Na$_2$SO$_4$, filtered and evaporated to dryness to yield 80 mg crude product. Crude product was purified on silica gel column using 2 M ammonia in methanol:dichloromethane (5:95) as a solvent system to yield 47 mg (14.2%) final pure product. MS (ESI) m/z 332.1 (M+H$^+$). $^1$H NMR (CDCl$_3$) δ 7.91 (d, J=6.84 Hz, 1 H), 7.8 (d, J=8.29 Hz, 2 H), 7.69 (s, 1 H), 7.33 (d, J=8.28 Hz, 2H), 7.28 (s, 1 H), 6.53 (dd, J=6.88 Hz, 1.52 Hz, 1 H), 6.4 (d, J=15.84 Hz, 1 H), 6.2 (dt, J=15.76, 6.88, 1 H), 2.74–2.32 (m, 15 H). HRMS: MH$^+$ calcd for C$_{22}$H$_{26}$N$_3$ 332.2127; found, 332.2119. Analysis: Calc'd for C$_{22}$H$_{25}$N$_3$·H$_2$O; C, 75.61; H, 7.79; N, 12.02. Found: C, 75.77; H, 7.07; N, 11.87.

EXAMPLE 41

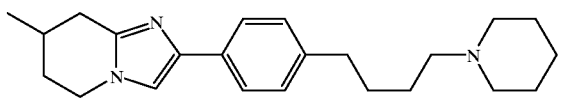

7-Methyl-2-[4-(4-piperidin-1-yl-butyl)-phenyl]-5,6,
7,8-tetrahydro-imidazo[1,2-a]pyridine $K_i$=27 nM Step A A mixture of 1-bromo-3-butene (1.35 g, 10 mmol) and piperidine (1.70 g, 20 mmol) neat was refluxed under nitrogen atmosphere for 3 h. Cooled to RT, filtered and dissolved into ethyl ether (40 mL). Then solution was washed with water (2×30 mL) and dried over anhydrous $Na_2SO_4$, filtered and evaporated to dryness to yield 1.3 g (74.15%) oily 1-piperidyl-3-butene.

Step B

A mixture of bromo product from (Example 38, Step A) (1.21 g, 4.2 mmol), 1-piperidyl-3-butene from Step A above (0.760 g, 5.46 mmol), palladium(II) acetate (95 mg, 0.42 mmol) and triphenylphosphine (221 mg, 0.84 mmol) was dissolved in triethylamine (53.2 g, 52.5 mmol) under nitrogen atmosphere. Dimethyl fomamide (5 mL) was added to dissolve all ingredients and refluxed for 24 h. The reaction mixture was cooled to room temperature and diluted with ethyl acetate (150 mL). Filtered the solution to remove solid suspension. The filtrate was washed with water (2×200 mL). Dried over anhydrous $Na_2SO_4$, filtered and evaporated to dryness to yield 1.4 g brownish yellow crude product. Crude product was purified on silica gel column using ethanol dichloromethane (5:95) yielding 0.80 g (55.2%) pure product.

Step C

Olefin from Step B above (100 mg, 0.29 mmol) was dissolved into methanol (20 mL) and added platinum(IV) oxide (20 mg). The resulting mixture was hydrogenated in Parr bottle at 50 psi hydrogen pressure for 32 h. Reaction mixture was filtered and evaporated to dryness to yield 60 mg (59%) of the final product. MS (ESI) m/z 352.1 (M+H$^+$). $^1$H NMR (CD$_3$OD) δ 7.75 (s, 1 H), 7.63 (d, J=7.5 Hz, 2 H), 7.39 (d, J=7.5 Hz, 2 H), 4.2 (m, 2 H), 3.6–1.5 (m, 2 H), 1.23 (d, J=6.06 Hz, 3 H). HRMS: MH$^+$ calcd for $C_{23}H_{34}N_3$, 352.2753; found, 352.2749. Analysis: Calc'd for $C_{23}H_{33}N_3$; C, 78.58; H, 9.46; N, 11.95. Found: C, 63.66; H, 9.18; N, 7.70.

EXAMPLE 42

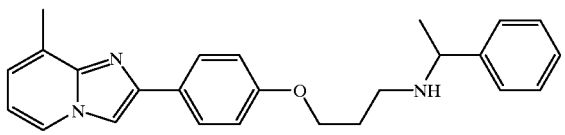

2-(4-alpha-Methylbenzylaminopropoxyphenyl)-8-
methylimidazo[1,2-a]pyridine $K_i$=1000 nM This compound was prepared according to the procedure described in Example 1 of U.S. Pat. No. 4,727,145. using 2-(4-chloropropoxyphenyl)-8-methylimidazo[1,2-a]pyridine and alpha-methylbenzylamine instead of 2-(4-chloropropoxyphenyl)-imidazo[1,2-a]pyridine and dibutylamine respectively.

Analysis: Calc'd for $C_{25}H_{27}N_3O$ 3HCl; C, 6.11; H, 60.8; N, 8.49. Found: C, 6.51; H, 60.43; N, 8.36

Example 43

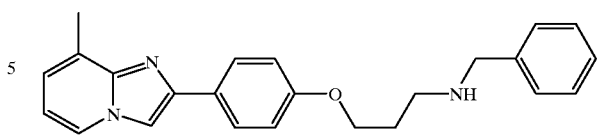

2-(4-Benzylaminopropoxyphenyl)-8-methylimidazo
[1,2-a]pyridine $K_i$=1000 nM

This compound was prepared according to the procedure described in Example 1 of U.S. Pat. No. 4,727,145. using 2-(4-chloropropoxyphenyl)-8-methylimidazo[1,2-a]pyridine and aniline instead of 2-(4-chloropropoxyphenyl)-imidazo[1,2-a]pyridine and dibutylamine respectively.

Analysis: Calc'd for $C_{24}H_{25}N_3O$ 3HCl; C, 5.87; H, 59.95; N, 8.74. Found: C, 5.7; H, 59.81; N, 8.59

Example 44

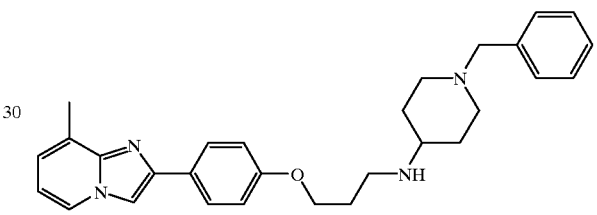

2-[4-[N-[(1-Benzylpiperidino)amino]propoxy]
phenyl]-8-methylimidazo[1,2-a]pyridine $K_i$=150 nM This compound was prepared according to the procedure described in Example 1 of U.S. Pat. No. 4,727,145. using 2-(4-chloropropoxyphenyl)-8-methylimidazo[1,2-a]pyridine and 4-amino-N-benzylpiperidine instead of 2-(4-chloropropoxyphenyl)-imidazo[1,2-a]pyridine and dibutylamine respectively.

Example 45

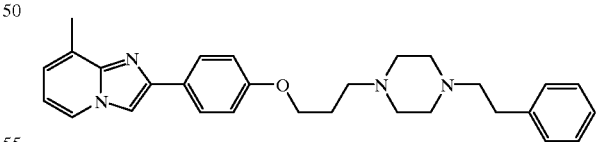

2-[4-[3-(4-Phenethylpiperazino)propoxy]phenyl]-8-
methylimidazo[1,2-a]pyridine $K_i$=500 nM This compound was prepared according to the procedure described in Example 1 of U.S. Pat. No. 4,727,145. using 2-(4-chloropropoxyphenyl)-8-methylimidazo[1,2-a]pyridine and N-phenethylpiperazine instead of 2-(4-chloropropoxyphenyl)-imidazo[1,2-a]pyridine and dibutylamine respectively.

Example 46

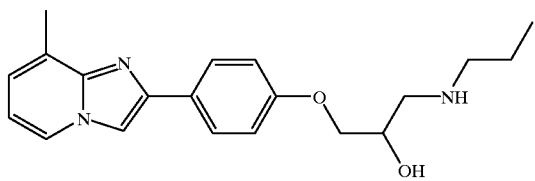

2-[4-(2-hydroxy-3-propylaminopropoxy)phenyl]-8-methylimidazo[1,2-a]pyridine $K_i$=1000 nM Step A Preparation of alpha bromo-4-hydroxyacetophenone
 4-Acetylphenol (20 g) in ether (200 mL) was treated with bromine (6.8 mL) and stirred at ambient temperature for 18 hours. The solution was poured into saturated sodium bicarbonate, stirred for 30 minutes and the organic layer separated. The organic portion was washed with saturated sodium bicarbonate, dried over magnesium sulfate, filtered and evaporated to afford the title compound (30 g).

Step B Preparation of 2-[4-hydroxyphenyl]-8-methylimidazo[1,2-a]pyridine

The product of step A (30 g) and 2-aminopicoline (15 mL) in ethanol (200 mL) was heated at reflux temperature for 4 hours then cooled to ambient temperature. The resulting precipitate containing the title compound was isolated via filtration (27 g).

Step C Preparation of 2-[4-[(2,3-Epoxy)propoxy]phenyl]-8-methylimidazo[1,2-a]pyridine The product of Step B (27 g) in methanol (500 mL) was treated with potassium hydroxide (14 g) and stirred at ambient temperature for 2 hours. To this solution was then added epichlorohydrin (9.4 mL) and the mixture stirred for an additional 48 hours. The reaction mixture was diluted with dichloromethane, filtered and the filtrate washed with water, dried, sodium sulfate filtered and evaporated to afford the title compound (18.2 g).

Step D Preparation of 2-[4-(2-hydroxy-3-propylaminopropoxy)phenyl]-8-methylimidazo[1,2-a]pyridine The product of Step C (5.0 g) and propylamine (20 mL) was heated at 40° C. for 18 hours. The reaction was cooled to ambient temperature evaporated and the residue purified via silica gel chromatography (dichloromethane/methanol) to give the title compound which was converted to a HCl salt upon treatment with HCl/methanol.

Analysis: Calc'd for $C_{20}H_{25}N_3O_2$ HCl $H_2O$; C, 7.16; H, 60.98; N, 10.67. Found: C, 7.31; H, 60.86; N, 10.92

Example 47

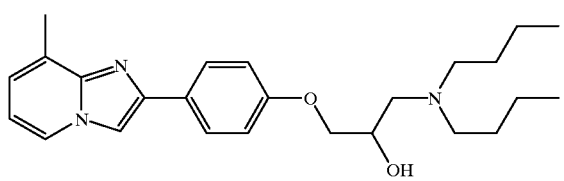

2-(4-Dipropylamino(2-hydroxy)propoxyphenyl)-8-methylimidazo[1,2-a]pyridine $K_i$=500 nM The title compound was prepared by reacting the product of Step C, Example 25 with dibutylamine.

Analysis: Calc'd for $C_{23}H_{31}N_3O_2$ 2HCl; C, 7.32; H, 60.79; N, 9.25. Found: C, 6.95; H, 0.81; N, 9.06

Example 48

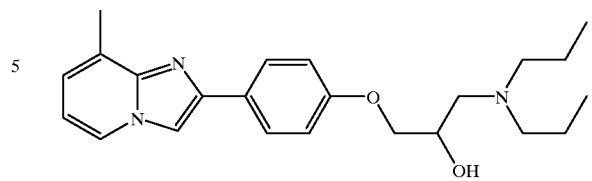

2-(4-Dibutylamino(2-hydroxy)propoxyphenyl)-8-methylimidazo[1,2-a]pyridine $K_i$=1000 nM The title compound was prepared by reacting the product of Step C, Example 25 with dipropylamine.

Analysis: Calc'd for $C_{25}H_{35}N_3O_2$ 2HCl; C, 7.73; H, 62.23; N, 8.71. Found: C, 7.82; H, 62.05; N, 8.47

Example 49

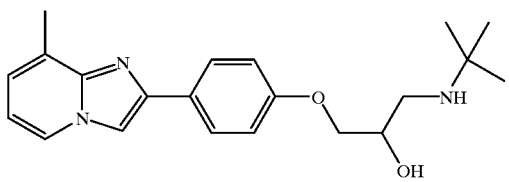

2-(4-(2-hydroxy-3-(1,1-Dimethylethyl)aminopropoxy)phenyl)-8-methylimidazo[1,2-a]pyridine $K_i$=1000 nM The title compound was prepared by reacting the product of Step C, Example 25 with 1,1-dimethylethylamine.

Analysis: Calc'd for $C_{21}H_{27}N_3O_2$ 2HCl; C, 6.86; H, 59.16; N, 9.85. Found: C, 6.66; H, 59.04; N, 9.74

Example 50

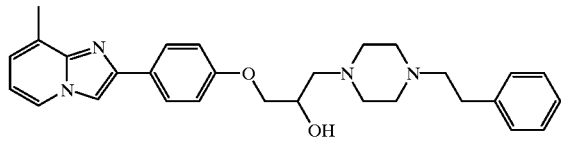

2-[4-[2-Hydroxy-3-(4-phenethylpiperazino)propoxy]phenyl]-8-methylimidazo[1,2-a]pyridine $K_i$=1000 nM 2-[4-[(3-Chloro-2-hydroxy)propoxy]phenyl]-8-methylimidazo[1,2-a]pyridine (5.0 g) in ethanol (10 mL) and N-phenethylpiperazine (1.4 g) were heated at 60° C. for 18 hours. The reaction mixture was cooled to ambient temperature, evaporated and purified via silica gel chromatography (dichloromethane/methanol) to give the title compound which was converted to a hydrochloride salt upon treatment with HCl/methanol. M.p. 225–228° C.

Example 51

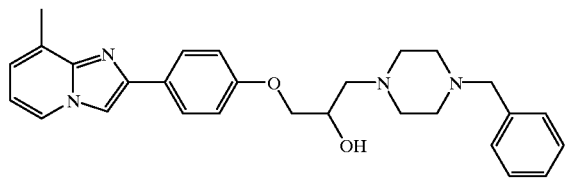

2-[4-[2-Hydroxy-3-(4-benzylpiperazino)propoxy]
phenyl]-8-methylimidazo[1,2-a]pyridine $K_i$=5000
nM 2-[4-[(3-Chloro-2-hydroxy)propoxy]phenyl]-8-methylimidazo[1,2-a]pyridine (5.0 g) in ethanol (10 mL) and N-benzyl-4-aminopiperidine (1.4 g) were heated at 60° C. for 18 hours. The reaction mixture was cooled to ambient temperature, evaporated and purified via silica gel chromatography (dichloromethane/methanol) to give the title compound which was converted to a hydrochloride salt upon treatment with HCl/methanol.

Example 52

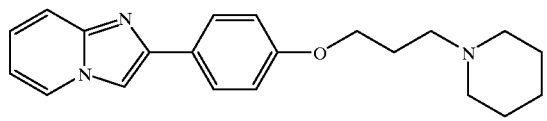

2-[4-(3-Piperidin-1-yl-propoxy)-phenyl]-imidazo[1,
2-a]pyridine $K_i$=5 nM

The product of Example 16 Step A (60 mg) and piperidine (1.0 mL) were heated at 100° C. for 1.5 hours. The reaction was cooled to ambient temperature and partitioned between ethyl acetate (10 mL) and saturated sodium bicarbonate solution (10 mL). The aqueous portion was extracted with a fresh portion of ethyl acetate (10 mL) and the organic portions combined and washed with brine (10 mL). The organic portions were dried over magnesium sulfate, filtered and evaporated. The residue was purified via silica gel chromatography (dichloromethane/methanol) to give the title compound (60 mg). $^1$H-NMR (CD$_3$OD) δ8.30 (m, 1H), 8.00 (s, 1H), 7.74 (m, 2H), 7.43 (m, 1H), 7.20 (m, 1H), 6.90 (m, 2H), 6.80 (m, 1H), 3.98 (t, J=6.0 Hz, 2H), 2.47 (m, 6H), 1.93 (m, 2H), 1.55 (m, 4H), 1.41 (m, 2H)

Example 53

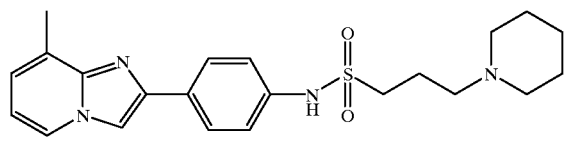

3-Piperidin-1-yl-propane-1-sulfonic acid [4-(8-methyl-imidazo[1,2-a]pyridin-2-yl)-phenyl]-amide
$K_i$=630 nM Step A Preparation of 3-Chloro-propane-1-sulfonic acid [4-(8-methyl-imidazo[1,2-a]pyridin-2-yl)-phenyl]-amide To a suspension of the product of Example 27 Step B (195 mg) in N,N-dimethylformamide (2 mL) was added triethylamine (0.12 mL) and the mixture cooled to 0° C. 3-chloropropanesulfonyl chloride (0.11 mL) was added dropwise and the mixture stirred for 1.5 hours before the addition of H$_2$O (2 mL). The reaction mixture was partitioned between H$_2$O (15 mL) and ethyl acetate (15 mL). The aqueous layer was brought to pH=9-10 with saturated sodium bicarbonate solution and extracted with ethyl acetate (2×). The combined organic layers were dried over magnesium sulfate, decanted, and evaporated. The residue was purified via silica gel chromatography (dichloromethane/methanol) to give the title compound (210 mg).

Step B Preparation of 3-Piperidin-1-yl-propane-1-sulfonic acid [4-(8-methyl-imidazo[1,2-a]pyridin-2-yl)-phenyl]-amide The product of Step A (65 mg) and piperidine (1.0 mL) were heated at 100° C. for 1.5 hours. The reaction was cooled to ambient temperature and partitioned between ethyl acetate (15 mL) and saturated sodium bicarbonate solution (15 mL). The aqueous portion was extracted with a fresh portion of ethyl acetate (15 mL) (2×) and the organic portions combined and washed with brine (15 mL). The organic portions were dried over magnesium sulfate, filtered and evaporated. The residue was purified via silica gel chromatography (dichloromethane/methanol) to give the title compound (26 mg).). $^1$H-NMR (CD$_3$OD) δ $^1$H-NMR (CD$_3$OD) δ8.14 (d, J=7.0 Hz, 1H), 8.00 (s, 1H), 7.81 (m, 2H), 7.23 (m, 2H), 6.98 (m, 1H), 6.70 (t, J=7.0 Hz, 1H), 3.07 (m, 2H), 2.49 (s, 3H), 2.31 (m, 6H), 1.87 (m, 2H), 1.44 (m, 4H), 1.33 (m, 2H).

Example 54

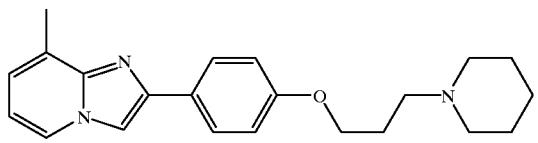

2-(4-Piperidinopropoxyphenyl)-8-methylimidazo[1,
2-a]pyridine $K_i$=1 nM

This compound was prepared according to the procedure described in Example 1 of U.S. Pat. No. 4,727,145 or *J. Med. Chem.* 188, 31, 2221 et seq., above using 2-(4-chloropropoxyphenyl)-8-methylimidazo[1,2-a]pyridine and piperidine instead of 2-(4-chloropropoxyphenyl)-imidazo[1,2-a]pyridine and dibutylamine respectively. Analysis: Calc'd for C$_{22}$H$_{27}$N$_3$O 3HCl 1H$_2$O; C, 6.76; H, 55.41; N, 8.81. Found: C, 6.63; H, 55.02; N, 8.55.

Example 55

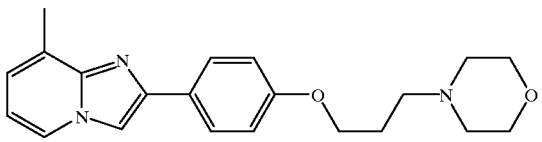

2-(4-Morpholinopropoxyphenyl)-8-methylimidazo
[1,2-a]pyridine $K_i$=25 nM

This compound was prepared according to the procedure described in Example 1 of U.S. Pat. No. 4,727,145 or *J. Med. Chem.* 188, 31, 2221 et seq., using 2-(4- chloropropoxyphenyl)-8-methylimidazo[1,2-a]pyridine and morpholine instead of 2-(4-chloropropoxyphenyl)-imidazo [1,2-a]pyridine and dibutylamine respectively. Analysis: Calc'd for $C_{21}H_{25}N_3O_2$ 3HCl 1.0$H_2O$; C, 6.31; H, 52.67; N, 8.78. Found: C, 6.69; H, 52.87; N, 8.89.

F. Biological Examples

In the present invention receptor binding was determined using the human histamine $H_3$ receptor (See Lovenberg et al *Mol. Pharmacol.* 1999, 1107). Screening using the human receptor is particularly important for the identification of new therapies for the treatment of human disease. Conventional binding assays for example are determined using rat synaptosomes (Garbarg et al *J. Pharmacol. Exp. Ther.* 1992, 263, 304), rat cortical membranes (West et al *Mol. Pharmacol.* 1990, 610), and guinea pig brain (Korte et al *Biochem. Biophys. Res. Commun.* 1990, 978). Only limited studies have been performed previously using human tissue but these allude to significant differences in the pharmacology of rodent and primate receptors (West et al *Eur. J. Pharmacol.* 1999, 233).

Biological Example 1

1(A) Transfection of Cells with Human Histamine Receptor

A 10 cm tissue culture dish with a confluent monolayer of SK-N-MC cells was split two days prior to transfection. Using sterile technique the media was removed and the cells were detached from the dish by the addition of trypsin. One fifth of the cells were then placed onto a new 10 cm dish. Cells were grown in a 37° C. incubator with 5% $CO_2$ in Minimal Essential Media Eagle with 10% Fetal Bovine Serum. After two days cells were approximately 80% confluent. These were removed from the dish with trypsin and pelleted in a clinical centrifuge. The pellet was then re-suspended in 400 μL complete media and transferred to an electroporation cuvette with a 0.4 cm gap between the electrodes (Bio-Rad #165–2088). One microgram supercoiled $H_3$ receptor cDNA was added to the cells and mixed. The voltage for the electroporation was set at 0.25 kV, the capacitance is set at 960 μF.

After electroporation the cells were diluted into 10 mL complete media and plated onto four 10 cm dishes. Due to the variability in the efficiency of electroporation, four different concentrations of cells were plated. The ratios used were: 1:20, 1:10, and 1:5, with the remainder of the cells being added to the fourth dish. The cells were allowed to recover for 24 hours before adding the selection media (complete media with 600 μg/ml G418). After 10 days dishes were analyzed for surviving colonies of cells. Dishes with well-isolated colonies were used. Cells from individual colonies were isolated and tested. SK-N-MC cells were used because they give efficient coupling for inhibition of adenylate cyclase. The clones that gave the most robust inhibition of adenylate cyclase in response to histamine were used for further study.

1(B) [$^3$H]-N-methylhistamine Binding

Cell pellets from histamine $H_3$ receptor-expressing SK-N-MC cells were homogenized in 20 mM TrisHCl/0.5 mM EDTA. Supernatants from a 800 g spin were collected, reccentrifuged at 30,000 g for 30 minutes. Pellets were rehomogenized in 50 mM Tris/5 mM EDTA (pH 7.4). Membranes were incubated with 0.8 nM [$^3$H]-N-methylhistamine plus/minus test compounds for 45 minutes at 25° C. and harvested by rapid filtration over GF/C glass fiber filters (pretreated with 0.3% polyethylenimine) followed by four washes with ice cold buffer. Filters were dried, added to 4 mL scintillation cocktail and then counted on a liquid scintillation counter. Non-specific binding was defined with 10 μM histamine according to Chen and Prusoff, *Biochem. Pharmacol.* 1973, 22:3099. $K_i$ values were calculated based on a $K_D$ of 800 μM and a ligand concentration ([L]) of 800 μM according to the formula: $K_i=(IC_{50})/(1+([L]/(K_D)))$. $K_i$ values are provided in the examples above.

F. Other Embodiments

The features and advantages of the invention are apparent to one of ordinary skill in the art. Based on this disclosure, including the summary, detailed description, background, examples, and claims, one of ordinary skill in the art will be able to make modifications and adaptations to various conditions and usages. These other embodiments are also within the scope of the invention.

What is claimed is:

1. A compound of formula (I)(A):

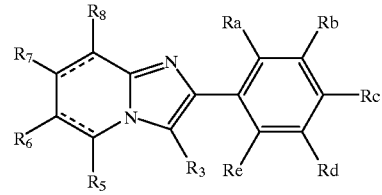

wherein both dashed lines complete a carbon-carbon double bond, or both are absent;

$R_3$ is H, $C_{1-6}$ alkyl, phenyl, or benzyl;

each of $R_5$, $R_6$, $R_7$ and $R_8$ is independently H, $C_{1-6}$ alkyl, $C_{1-6}$ alkoxy, halo, or amino, with the proviso that $R_7$ is methyl when both dashed lines complete a carbon-carbon double bond;

one of $R_a$, $R_b$, $R_c$, $R_d$, and $R_e$ is —WYZ and the others are independently selected from H, $C_{1-6}$ alkyl, $C_{1-6}$ alkoxy, halo, and amino;

W is O—$R_9$, wherein $R_9$ is $C_{1-6}$ alkylene, $C_{2-6}$ alkynylene, phenylene, or $C_{2-5}$ heterocyclic bivalent radical;

Y is absent, $C_{1-6}$ alkyl, $C_{2-6}$ alkynyl, $C_{2-6}$ alkenyl, or $C_{1-6}$ alkoxy;

Z is $C_{2-8}$ heterocyclic radical with at least one basic nitrogen atom in the ring, optionally including in the ring up to 3 additional heteroatoms or moieties independently selected from O, C=O, N, NH, NG, S, SO, and $SO_2$, wherein G is $R_{15}$, $COR_{15}$, $COOR_{15}$, $SO_2R_{15}$, $SO_2N$ or $CSR_{15}$; and $R_{15}$ is $C_{1-6}$ alkyl, $C_{2-6}$ alkynyl, $C_{2-6}$ alkenyl, $C_{3-7}$ cycloalkyl, or $C_{4-7}$ cycloalkenyl; and each of the above hydrocarbyl or heterocyclic groups being optionally substituted with between 1 and 3 substituents selected from $C_{1-3}$ alkyl, halo, hydroxy, $C_{2-5}$ heterocyclic radical, phenyl, and phenyl($C_{1-3}$ alkyl); and wherein each of the above heterocyclic groups may be attached to the rest of the molecule by a carbon atom or a heteroatom;

or a pharmaceutically acceptable salt, amide, ester, or hydrate thereof.

2. A compound of claim 1, wherein Z comprises piperidyl, morpholinyl, piperazinyl, pyrrolidyl, or a $C_{6-8}$ cycloalkylimino radical.

3. A compound of claim 1, wherein W is hydroxy-substituted $C_{2-4}$ alkoxy or $C_{2-4}$ alkoxy.

4. A compound of claim 1, wherein W comprises propoxy or ethoxy.

5. A compound of claim 1 wherein at least one of $R_a$, $R_b$, $R_d$, and $R_e$ is methyl.

6. A compound of claim 1, wherein each of $R_5$, $R_6$, and $R_8$ is independently H, methyl, ethyl, methoxy, ethoxy, fluoro, or chloro; or wherein one of $R_a$, $R_b$, $R_c$, $R_d$, and $R_e$ is WZ and the others are independently selected from H, methyl, ethyl, methoxy, ethoxy, fluoro, or chloro.

7. A compound of claim 1, wherein $R_a$ or $R_e$ is methyl, fluoro, or methoxy.

8. A compound of claim 1, wherein
$R_3$ is H or methyl;
each of $R_b$ and $R_d$ is independently H, methyl, or methoxy;
$R_8$ is H, methyl, fluoro, or chloro;
each of $R_5$ and $R_6$ is H;
each of $R_a$ or $R_e$ is independently H, methyl, fluoro, or chloro;
W is $C_{2-4}$ alkoxy; and
Z is pyrrolidyl, piperidyl, morpholinyl, piperazinyl, or (piperidyl)-piperidyl.

9. A compound of claim 2, selected from 2-(4-Piperidinopropoxy-2-methylphenyl) -7-methylimidazo[1,2-a]pyridine; 2-(4-hexamethyleneiminopropoxyphenyl)-7-methylimidazo[1,2-a]pyridine; 2-(4Pyrrolidinopropoxyphenyl)-7-methylimidazo[1,2-a] pyridine; and 2-(4-Piperidinopropoxyphenyl)-7-methylimidazol[1,2-a]pyridine.

10. A compound selected from 2-[4-(3-Piperidin-1-yl-propoxy) -phenyl]-5,6,7,8-tetrahydro-imidazo[1,2-a] pyridine; and 7-methyl-2-[2-methyl-4-(3-piperidin-1-yl-propoxy) -phenyl]-5,6,7,8-tetrahydro-imidazo[1,2-a]pyridine.

11. A compound of claim 9, having the formula 2-(4-Piperidinopropoxyphenyl) -7-methylimidazo[1,2-a] pyridine.

12. A pharmaceutical composition comprising a compound of claim 1 and a pharmaceutically-acceptable carrier.

13. A pharmaceutical composition of claim 12, wherein said compound has a formula wherein $R_3$ is H or methyl; each of $R_b$ and $R_d$ is independently H, methyl, or methoxy; $R_8$ is H, methyl, fluoro, or chloro; each of $R_5$ and $R_6$ is H; each of $R_a$ or $R_e$ is independently H, methyl, fluoro, or chloro; W is $C_{2-4}$ alkoxy; and Z is pyrrolidyl, piperidyl, morpholinyl, piperazinyl, or (piperidyl)-piperidyl.

14. A pharmaceutical composition of claim 13, wherein said compound has a formula selected from 2-(4-Piperidinopropoxy -2-methphenyl)-7-methylimidazo[1,2-a]pyridine; 2-(4- hexamethyleneiminopropoxphenyl)-7-methylimidazo [1,2-a]pyridine; 2-(4-Pyrrolidinopropoxyphenyl)-7- methylimidazo [1,2-a]pyridine; 2-(4-Piperidinopropoxyphenyl)-7-methylimidazo [1,2-a]pyridine; and 7-methyl-2-[2-methyl-4-(3-piperidin-1-yl-propoxy)-phenyl]-5,6,7,8-tetrahydro-imidazo[1 2-a]pyridine.

15. A pharmaceutical composition of claim 13, wherein said compound is 2-(4-Piperidinopropoxyphenyl)-7-methylimidazo[1,2-a]pyridine.

16. A method for treating a patient with a central nervous system disorder selected from sleep/wake disorders, arousal/vigilance disorders, dementia, Alzheimer's disease, epilepsy, narcolepsy, eating disorders, motion sickness, vertigo, attention deficit hyperactivity disorder, learning and memory disorders, cognitive impairment, schizophrenia, allergic rhinitis and asthma, said method comprising administering to the patient a pharmaceutically-effective amount of a compound of formula (I):

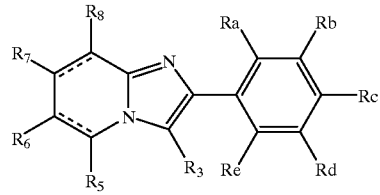

wherein both dashed lines complete a carbon-carbon double bond, or both are absent;
$R_3$ is H, $C_{1-6}$ alkyl, phenyl, or benzyl;
each of $R_5$, $R_6$, $R_7$ and $R_8$ is independently H, $C_{1-6}$ alkyl, $C_{1-6}$ alkoxy, halo, or amino;
one of $R_a$, $R_b$, $R_c$, $R_d$ and $R_e$ is —WYZ and the others are independently selected from H, $C_{1-6}$ alkyl, $C_{1-6}$ alkoxy, halo, and amino;
W is O—$R_9$, wherein $R_9$ is $C_{1-6}$ alkylene, $C_{2-5}$ alkynylene, pheneylene, or $C_{2-5}$ heterocyclic bivalent radical, and $R_{10}$ is H, $C_{1-6}$ alkyl, $C_{2-6}$ alkynyl, $C_{2-6}$ alkenyl, phenyl, or $C_{2-5}$ heterocyclic radical;
Y is absent, $C_{1-6}$ alkyl, $C_{2-6}$ alkynyl, $C_{2-6}$ alkenyl, or $C_{1-6}$ alkoxy; Z is $C_{2-8}$ heterocyclic radical with at least one basic nitrogen atom in the ring, optionally including in the ring up to 3 additional heteroatoms or moieties independently selected from O, C=O, N, NH, NG, S, SO, and $SO_2$, wherein G is $R_{15}$, $COR_{15}$, $COOR_{15}$, $SO_2R_{15}$, $SO_2N$ or $CSR_{15}$; and $R_{15}$ is $C_{1-6}$ alkyl, $C_{2-6}$ alkynyl, $C_{2-6}$ alkenyl, $C_{3-7}$ cycloalkyl, or $C_{4-7}$ cycloalkenyl; and
each of the above hydrocarbyl or heterocyclic groups being optionally substituted with between 1 and 3 substituents selected from $C_{1-3}$ alkyl, halo, hydroxy, $C_{2-5}$ heterocyclic radical, phenyl, and phenyl($C_{1-3}$ alkyl); and wherein each of the above heterocyclic groups may be attached to the rest of the molecule by a carbon atom or a heteroatom;
or a pharmaceutically acceptable salt, amide, ester, or hydrate thereof.

17. A method of claim 16, wherein said compound is selected from 2-[4-[2-(1-Methyl)-2-pyrrolidino]ethoxy-3-methylphenyl]imidazo[1,2-a]pyridine; 2-(4-Piperidinopropoxy -2-methylphenyl)-7-methylimidazo[1,2-a]pyridine; 2-(4-hexamethyleneiminopropoxyphenyl)-7-methylimidazo [1,2-a]pyridine; 2-(4-Pyrrolidinopropoxyphenyl)-7-methylimidazo [1,2-a] pyridine; 2-(4-Piperidinopropoxyphenyl)-7-methylimidazo [1,2-a]pyridine; 2-[4-(3-Piperidin-1-yl-propoxy)-pheny phenyl]-imidazo[1,2-a]pyridine; 2-(4-Piperdinopropoxyphenyl)-8-methylimidazo [1,2-a]pyridine; 2-[4-(3-Piperidin-1 -yl-propoxy)-phenyl ]-5,6,7,8-tetrahydro-imidazo[1,2-a]pyridine; 7-methyl-2-[2-methyl -4-(3-piperidin-1-yl-propoxy)-phenyl]-5,6,7,8-tetrahydro-imidazo [1,2-a]pyridine; 2-(4-piperidino-propoxyphenyl)-8-methylimidazo [1,2-a]pyridine; and 2-(4-morpholinopropoxyphenyl) -8-methylimidazo[1,2-a]pyridine.

18. A method of claim 16, wherein said disorder is selected from sleep/wake disorders, arousal/vigilance disorders, attention deficit hyperactivity disorder, and learning and memory disorders.

19. A method for treating a patient with an upper airway allergic response, said method comprising administering to the patient a pharmaceutically-effective amount of a compound of formula (I):

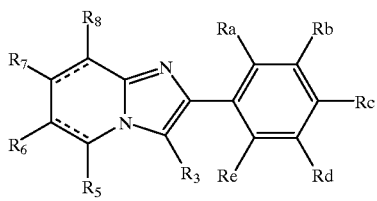

wherein both dashed lines complete a carbon-carbon double bond, or both are absent;

$R_3$ is H, $C_{1-6}$ alkyl, phenyl, or benzyl;

each of $R_5$, $R_6$, $R_7$ and $R_8$ is independently H, $C_{1-6}$ alkyl, $C_{1-6}$ alkoxy, halo, or amino;

one of $R_a$, $R_b$, $R_c$, $R_d$, and $R_3$ is —WYZ and the others are independently selected from H, $C_{1-6}$ alkyl, $C_{1-6}$ alkoxy, halo, and amino;

W is O—$R_9$, wherein $R_9$ is $C_{1-6}$ alkylene, $C_{2-6}$ alkynylene, $C_{2-5}$ alkenylene, phenylene, or $C_{2-5}$ heterocyclic bivalent radical, and $R_{10}$ is H, $C_{1-6}$ alkyl, $C_{2-6}$ alkynyl, $C_{2-6}$ alkenyl, phenyl, or $C_{2-5}$ heterocyclic radical;

Y is absent, $C_{1-6}$ alkyl, $C_{2-6}$ alkynyl, $C_{2-6}$ alkenyl, or $C_{1-6}$ alkoxy;

Z is $C_{2-8}$ heterocyclic radical with at least one basic nitrogen atom in the ring, optionally including in the ring up to 3 additional heteroatoms or moieties independently selected from O, C=O, N, NH, NG, S, SO, and $SO_2$, wherein G is $R_{15}$, $COR_5$, $COOR_{15}$, $SO_2R_{15}$, $SO_2N$ or $CSR_{15}$; and $R_{15}$ is $C_{1-6}$ alkyl, $C_{2-6}$ alkynyl, $C_{2-6}$ alkenyl, $C_{3-7}$ cycloalkyl, or $C_{4-7}$ cycloalkenyl; and each of the above hydrocarbyl or heterocyclic groups being optionally substituted with between 1 and 3 substituents selected from $C_{1-6}$ alkyl, halo, hydroxy, $C_{2-5}$ heterocyclic radical, phenyl, and phenyl($C_{1-3}$ alkyl); and wherein each of the above heterocyclic groups may be attached to the rest of the molecule by a carbon atom or a heteroatom;

or a pharmaceutically acceptable salt, amide, ester, or hydrate thereof.

20. A method of claim 19, wherein said compound is selected from 2-[4-[2-(1-Methyl)-2-pyrrolidino]ethoxy-3-methylphenyl]imidazo[1,2-a]pyridine; 2-(4-Piperidinopropoxy-2-methylphenyl)-7-methylimidazo[1,2-a]pyridine; 2-(4-hexamethyleneiminopropoxyphenyl)-7-methylimidazo[1,2-a]pyridine; 2-(4-Pyrrolidinopropoxyphenyl)-7-methylimidazo[1,2-a]pyridine; 2-(4-Piperidinopropoxyphenyl)-7-methylimidazo[1,2-a]pyridine; 2-[4-(3-Piperidin-1-yl-propoxy)-phenyl]-imidazo[1,2-a]pyridine; 2-(4-Piperidinopropoxyphenyl)-8-methylimidazo[1,2-a]pyridine; 2-[4-(3-Piperidin-1-yl-propoxy)-phenyl]-5,6,7,8-tetrahydro-imidazo[1,2-a]pyridine; 7-methyl-2-[2-methyl 4-(3-piperidin-1-yl-propoxy)-phenyl]-5,6,7,8-tetrahydro-imidazo[1,2-a]pyridine; 2-(4-piperidinopropoxyphenyl)-8-methylimidazo[1,2-a]pyridine; and 2-(4-morpholinopropoxyphenyl)-8-methylimidazo[1,2-a]pyridine.

21. A method of claim 19, wherein said compound is 2-(4-Piperidinopropoxyphenyl)-7-methylimidazo[1,2-a]pyridine.

* * * * *